US009004545B2

(12) United States Patent
Whitaker et al.

(10) Patent No.: US 9,004,545 B2
(45) Date of Patent: Apr. 14, 2015

(54) CLAMP FOR SANITARY FITTING

(75) Inventors: Carl T. Whitaker, Berthoud, CO (US); Bruce Williams, Fort Collins, CO (US); Ravikumar Narayanan, Fort Collins, CO (US); Francis J. Lombardi, III, Erie, CO (US); Kenneth R. Davis, Longmont, CO (US)

(73) Assignee: Nordson Corporation, Westlake, OH (US)

( * ) Notice: Subject to any disclaimer, the term of this patent is extended or adjusted under 35 U.S.C. 154(b) by 23 days.

(21) Appl. No.: 13/414,635

(22) Filed: Mar. 7, 2012

(65) Prior Publication Data

US 2012/0227221 A1 Sep. 13, 2012

Related U.S. Application Data

(60) Provisional application No. 61/450,088, filed on Mar. 7, 2011.

(51) Int. Cl.

| | |
|---|---|
| ***F16L 21/00*** | (2006.01) |
| ***A61M 39/10*** | (2006.01) |
| ***F16L 19/02*** | (2006.01) |
| ***F16L 23/04*** | (2006.01) |

(52) U.S. Cl.

CPC ........ *A61M 39/1011* (2013.01); *F16L 19/0218* (2013.01); *F16L 23/04* (2013.01); *F16L 2201/44* (2013.01)

(58) Field of Classification Search

USPC .............. 285/420, 419, 407; 24/16 PB, 17 A, 24/17 AP

See application file for complete search history.

(56) References Cited

U.S. PATENT DOCUMENTS

| | | | |
|---|---|---|---|
| 144,997 | A | 11/1873 | Mayall |
| 422,945 | A | 3/1890 | Jones |
| 784,979 | A | 3/1905 | Bruce |
| 1,441,154 | A | 1/1923 | Johnson |
| 3,021,584 | A | 2/1962 | Polanski |
| 3,352,582 | A | 11/1967 | Mankin et al. |
| 3,429,985 | A | 2/1969 | Czigler |
| 3,670,369 | A | 6/1972 | McIlroy, II |

(Continued)

FOREIGN PATENT DOCUMENTS

| | | |
|---|---|---|
| DE | 2265495 | 4/1980 |
| DE | 3215382 | 10/1983 |

(Continued)

OTHER PUBLICATIONS

International Search Report and Written Opinion dated May 8, 2012, PCT/US2012/028136, 12 pages.

(Continued)

*Primary Examiner* — Aaron Dunwoody
(74) *Attorney, Agent, or Firm* — Dorsey & Whitney LLP

(57) ABSTRACT

A clamp for sanitary fittings includes a clamp body formed of a first arcuate member and a second arcuate member movable about a hinge assembly from an open configuration to a closed, latched configuration. The hinge assembly detachably couples the first arcuate member to the second arcuate member. The hinge assembly includes an arcuate finger extending from an end of the first arcuate member, a pin-receiving recess formed within the arcuate finger, and a post formed on an end of the second arcuate member. Upon assembly, the arcuate finger cradles around the post and the post fits within the pin-receiving recess.

16 Claims, 19 Drawing Sheets

(56) References Cited

U.S. PATENT DOCUMENTS

| | | | |
|---|---|---|---|
| 3,705,737 A | 12/1972 | Westerlund et al. | |
| 3,913,187 A | 10/1975 | Okuda | |
| 4,020,277 A | 4/1977 | LaChance, Sr. et al. | |
| 4,082,917 A | 4/1978 | Hendrix | |
| 4,183,120 A | 1/1980 | Thorne | |
| 4,306,740 A | 12/1981 | Kleykamp et al. | |
| 4,386,752 A | 6/1983 | Pavlak et al. | |
| 4,483,556 A | 11/1984 | LiVolsi | |
| 4,485,530 A | 12/1984 | Begley et al. | |
| 4,502,186 A | 3/1985 | Clarke et al. | |
| 4,557,024 A | 12/1985 | Roberts et al. | |
| 4,663,807 A | 5/1987 | Bozzo | |
| 4,746,127 A | 5/1988 | Westhoff et al. | |
| 4,840,345 A | 6/1989 | Neil et al. | |
| D307,541 S | 5/1990 | Tres | |
| 4,942,886 A | 7/1990 | Timmons | |
| 5,024,405 A | 6/1991 | McGuire | |
| D319,298 S | 8/1991 | Due | |
| 5,157,815 A | 10/1992 | Dyer | |
| 5,227,139 A | 7/1993 | Wong | |
| 5,280,866 A | 1/1994 | Ueki | |
| D344,672 S | 3/1994 | Current | |
| 5,305,978 A | 4/1994 | Current | |
| 5,375,299 A | 12/1994 | Nagano | |
| 5,423,501 A | 6/1995 | Yu | |
| 5,540,465 A | 7/1996 | Sisk | |
| 5,590,859 A | 1/1997 | Lord | |
| 5,653,411 A | 8/1997 | Pico et al. | |
| D389,052 S | 1/1998 | Yamamoto | |
| 5,725,185 A | 3/1998 | Auclair | |
| 5,729,872 A * | 3/1998 | Ginocchio | 24/16 R |
| 5,740,844 A | 4/1998 | Miller | |
| D420,569 S | 2/2000 | Evans | |
| 6,030,006 A | 2/2000 | Lin | |
| 6,164,605 A | 12/2000 | Drake et al. | |
| 6,186,454 B1 | 2/2001 | Olsen | |
| 6,206,331 B1 | 3/2001 | Keith et al. | |
| 6,234,545 B1 | 5/2001 | Babuder et al. | |
| 6,266,852 B1 | 7/2001 | Tai | |
| 6,488,664 B1 | 12/2002 | Solomon et al. | |
| 6,505,639 B1 | 1/2003 | Navarro | |
| 6,523,866 B2 | 2/2003 | Lin | |
| D473,130 S | 4/2003 | Leung | |
| 6,708,377 B2 | 3/2004 | Maunder | |
| 6,742,223 B1 | 6/2004 | Chang | |
| 6,764,284 B2 | 7/2004 | Oehman, Jr. | |
| 6,840,782 B1 | 1/2005 | Borden et al. | |
| 6,978,973 B1 | 12/2005 | Gretz | |
| D537,334 S | 2/2007 | Lee | |
| 7,178,203 B2 | 2/2007 | Pearson et al. | |
| 7,284,731 B1 | 10/2007 | Johnson et al. | |
| 7,290,805 B2 | 11/2007 | Wu | |
| 7,309,218 B1 | 12/2007 | Lewis et al. | |
| 7,370,889 B2 | 5/2008 | Mauder et al. | |
| 7,384,078 B2 | 6/2008 | Cobb et al. | |
| 7,387,282 B2 | 6/2008 | Kovak | |
| D577,423 S | 9/2008 | Dole | |
| D584,604 S | 1/2009 | Baldwin | |
| 7,500,643 B2 | 3/2009 | Leone et al. | |
| D609,998 S | 2/2010 | Radle et al. | |
| 7,677,612 B2 | 3/2010 | Maunder | |
| 7,784,745 B2 | 8/2010 | Dodge | |
| 7,794,243 B1 | 9/2010 | Rzasa et al. | |
| 7,805,814 B2 | 10/2010 | Cho | |
| 7,832,420 B2 | 11/2010 | Hoskisson et al. | |
| 7,883,121 B2 | 2/2011 | Henry | |
| 7,900,324 B2 * | 3/2011 | Ginocchio | 24/272 |
| 8,246,095 B2 * | 8/2012 | Radle et al. | 294/165 |
| 8,294,583 B2 * | 10/2012 | Sayegh et al. | 340/572.9 |
| 2007/0001448 A1 | 1/2007 | Navarro | |
| 2008/0179469 A1 | 7/2008 | Leone et al. | |
| 2009/0119886 A1 | 5/2009 | Werth | |
| 2010/0060460 A1 * | 3/2010 | Zinner | 340/572.9 |
| 2010/0132165 A1 | 6/2010 | Shor et al. | |
| 2010/0229353 A1 | 9/2010 | Gayer et al. | |
| 2010/0230949 A1 | 9/2010 | Lake | |
| 2010/0327576 A1 | 12/2010 | Linhorst et al. | |
| 2011/0042947 A1 | 2/2011 | Hansen | |

FOREIGN PATENT DOCUMENTS

| | | |
|---|---|---|
| DE | 4427513 | 2/1996 |
| DE | 10128700 | 1/2003 |
| DE | 20307871 | 9/2003 |
| EP | 276640 | 8/1988 |
| EP | 1840439 | 6/2010 |
| EP | 1696164 | 10/2010 |
| EP | 1766279 | 12/2010 |
| GB | 2051213 | 1/1981 |
| GB | 2098297 | 11/1982 |
| WO | WO 99/061831 | 12/1999 |
| WO | WO 2004/023016 | 3/2004 |
| WO | WO 2009/051591 | 4/2009 |
| WO | WO 2010/126942 | 11/2010 |

OTHER PUBLICATIONS

Heavy Duty Clamp (STPP7707); http://wzsatai.en.made-in-china.com/product/iqxQNAVTqDhU/China-Heavy-Duty-Clamp-STPP7707-.html; date accessed: Sep. 24, 2010, 2 pages.

Sanitary Fittings (STU1107); http://wzsatai.en.made-in-china.com/product/CoJnSuUYhlkj/China-Sanitary-Fittings-STU1107-.html; date accessed: Sep. 24, 2010, 2 pages.

Quick Clamp with Ratchet Closure, KF-25 ISO-KF Flange Size NW-25, Aluminum Black Finish; Ideal Vacuum Products; http://www.pchemlabs.com/product.asp?pid=2582; date accessed: Sep. 24, 2010; 4 pages.

Value Plastics, Inc., a Nordson Company, Component Configurator for Sanitary Fitting, Clamp, http://www.valueplastics.com/search/search.aspx, published as early as Apr. 2009, 1 page.

* cited by examiner

CLAMP FOR SANITARY FITTING

CROSS REFERENCE TO RELATED APPLICATION

This application claims the benefit of priority pursuant to 35 U.S.C. §119(e) of U.S. provisional application No. 61/450,088 filed 7 Mar. 2011, entitled "Clamp for sanitary fitting", which is hereby incorporated herein by reference in its entirety.

TECHNICAL FIELD

This disclosure relates to clamps for use with sanitary fittings.

BACKGROUND

Maintaining sterility in manufacturing processes is often a concern. Receptacles with outlets provided by sanitary fittings are often required to interconnect with other sanitary fittings, typically connected to lengths of fluid transport tubing, for purposes of transferring contents from one receptacle to another. To ensure the transfer occurs under sterile conditions, the sanitary fittings are clamped together so that contents can be transferred without exposure to the external environment.

The information included in this Background section of the specification, including any references cited herein and any description or discussion thereof, is included for technical reference purposes only and is not to be regarded subject matter by which the scope of the invention as defined in the claims is to be bound.

SUMMARY

Implementations of a clamp for sanitary fittings disclosed herein may include a clamp body formed of a first arcuate member and a second arcuate member movable about a hinge assembly from an open configuration to a closed, latched configuration. In one exemplary implementation, the hinge assembly detachably couples the first arcuate member to the second arcuate member and enables relative rotation between the first and the second arcuate members from an open position to a closed position. The hinge assembly includes an arcuate finger extending from an end of the first arcuate member, a pin-receiving recess formed within the arcuate finger, and a post formed on an end of the second arcuate member. Upon assembly, the arcuate finger pin-receiving recess around the post and the post fits within the pin-receiving recess.

In some implementations, a latch finger may extend from one of the first and second arcuate members at an end opposite the hinge assembly. A retention cavity may be formed within an other of the first and second arcuate members at an end opposite the hinge assembly. The retention cavity is configured to receive and engage the latch finger when the clamp is in a closed position. The latch finger may define a plurality of teeth and the retention cavity may define a plurality of opposing teeth. When the clamp is in a closed position, one or more of the teeth on the latch finger may engage one or more of the teeth within the retention cavity. The clamp may include finger grips protruding from an outer surface of each of the arcuate members for moving the clamp between the opened and the closed position.

In another exemplary implementation, a clamp has a first arcuate member comprising a barrel structure and a second arcuate member comprising a pin structure. A relatively rigid but bendable tether is connected between the barrel structure and the pin structure when the first and second arcuate members are in an unassembled state. In the unassembled state, the tether guides assembly of the first arcuate member with the second arcuate member by guiding an establishment of a coupled engagement between the barrel structure and the pin structure. Upon establishment of the coupled engagement, the tether disconnects from either the barrel structure or the pin structure.

In a further exemplary implementation, a method of connecting two sanitary fittings to a gasket using a clamp is provided. The clamp has a first arcuate member defining an internal channel along an inner diameter thereof and a second arcuate member defining an internal channel along an inner diameter thereof. A hinge assembly is formed as part of an end of each of the first and second arcuate members and detachably couples the first arcuate member to the second arcuate member. The hinge assembly enables relative rotation between the first and the second arcuate members from an open position to a closed position. A latch finger extends from an end of the first arcuate member opposite the end forming the hinge assembly. An engagement structure extends from an end of the second arcuate member opposite the end forming the hinge assembly and is configured to engage with the latch finger to lock the clamp in the closed position. The method begins by inserting circular flange structures on two sanitary fittings and a gasket into the internal channel of the first arcuate member in the open position of the clamp with the gasket placed between the circular flange structures of each of the sanitary fittings. Next, the first and the second arcuate members are rotated relative to each other about the hinge assembly into the closed position such that the circular flange structures of each of the sanitary fittings and the gasket are received within the internal channel of the second arcuate member. In the closed position, a first stop surface of the first arcuate member adjacent the latch finger and a second stop surface of the second arcuate member adjacent the engagement structure abut and a third stop surface of the first arcuate member adjacent the hinge assembly and a fourth stop surface of the second arcuate member adjacent the hinge assembly abut to form a circular closure retaining the circular flange structures of each of the sanitary fittings and the gasket completely within the internal channels to provide a circular seal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Figure 1:
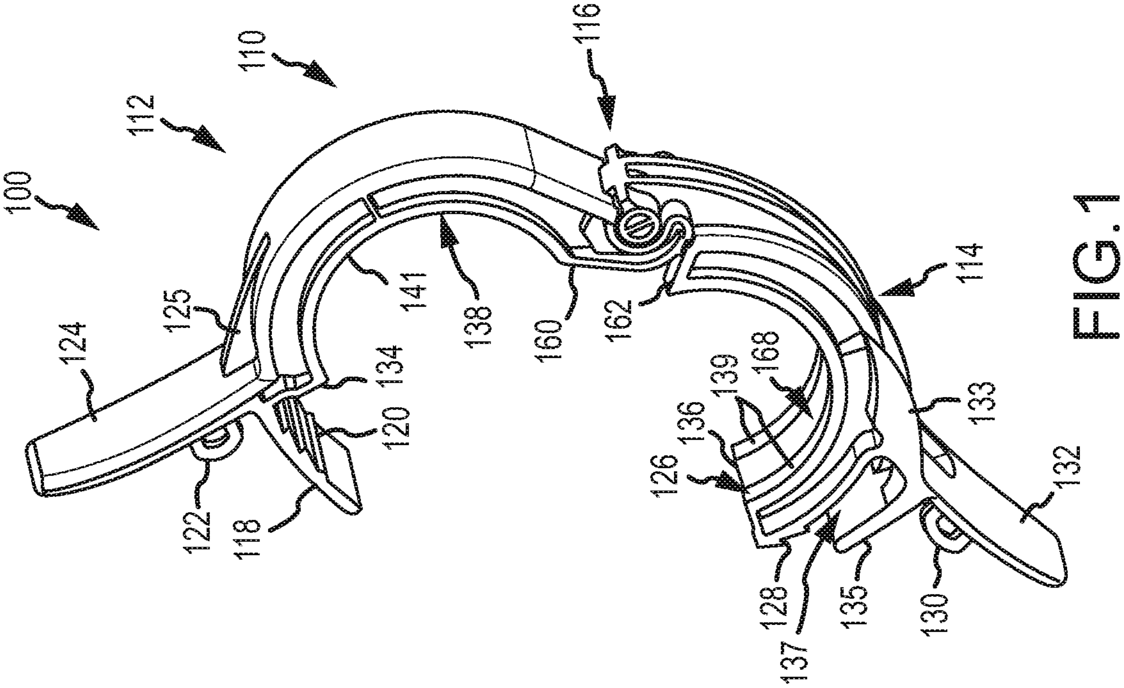
FIG. 1 is a back right isometric view of an implementation of a clamp in an open position.

FIG. 1 is a back right isometric view of a clamp 100 that may be used to join two sanitary fittings F (see FIG. 7) for the sterile transport of contents from one receptacle to another. A sanitary fitting on a receptacle may have a short cylindrical duct that extends from the receptacle and terminates with a flange. An opposing sanitary fitting with a corresponding flange may be positioned opposite the fitting attached to the receptacle and both flanges may be secured together by and within the clamp 100. Typically an annular silicone, rubber, or elastomeric gasket is placed between the flanges of the sanitary fittings in order to provide a fluid-tight seal. In other implementations, the clamp may be used to join two sanitary fittings used to connect two pieces of hose or other fluid tubing used to transport fluid from one receptacle to another. Such sanitary fittings may have a barbed end for attaching to the fluid tubing and a flange end for interfacing with an opposing flange end and configured to be held within a clamp. Again, a gasket is typically placed between the faces of the flanged ends.

The clamp 100 may establish a circular closure around a circular structure (e.g., a flange of a sanitary fitting) contained within an interior of the clamp 100 for providing equal sealing pressure around the entire circular structure. For example, the clamp 100 may provide equal sealing pressure between two sanitary fittings and a gasket arranged therebetween. Providing equal sealing pressure using the clamp 100 may establish a 360 degree seal between the components secured within the clamp 100. The clamp 100 may thus prevent over-compression of the sanitary fitting connection to the gasket, thereby avoiding catastrophic failure to the connection due to, for example, the gasket extruding outside of the sanitary fitting from the over-compression.

The clamp 100 may include a main body 110 formed of a first arcuate member 112 and a second arcuate member 114 detachably joined by a hinge assembly 116. The first arcuate member 112 may include a latch finger 118 with teeth 120, a first tie-receiving loop 122, a handle 124, and a reinforcement rib 125. The second arcuate member 114 may include a mating end 126 with teeth 128, a second tie receiving loop 130, a handle 132, and reinforcement ribs 133. The hinge assembly 116 may include a barrel structure 140 (FIG. 2) formed on the first arcuate member 112 of the clamp body and an pin structure 142 (FIG. 2) formed on the second arcuate member 114 of the clamp body 110.

The first arcuate member 112 of the main body 110 may form substantially half of the clamp 100. (See FIG. 3) An inner edge of the first arcuate member 112 may form a semi-circular arc segment spanning about 180 degrees. The latch finger 118 of the first arcuate member 112 may depend from a terminal end of the arc segment opposite the hinge assembly 116 and extend toward the mating end 126 of the second arcuate member 114 when the main body 110 is assembled. The latch finger 118 may depend from the end of the first arcuate member 112 or from a base portion of the handle 124 and may extend generally tangential to an outer wall of the first arcuate member 112 defining an outer diameter of the main body 110 of the clamp 100.

Along an inner wall the latch finger 118, one or a series of teeth 120 may be formed. The teeth 120 may face toward the main body 110 and may be configured to engage with the teeth 128 of the second arcuate member 114. The teeth 120 may extend along a portion of the latch finger 118 or substantially along the entire length of the latch finger 118. Each tooth of the teeth 120 may protrude as stepped ridges or barbs from the latch finger 118 and may taper downwardly towards the free end of the latch finger 118. However, the teeth 120 may be configured in any manner that enables the teeth 120 and 128 to establish an interfaced engagement.

A first tie-receiving loop 122 may be formed on a bottom portion of the handle 124 above the latch finger 118. The first tie-receiving loop 122 may define an opening that, for example, enables one end of a zip tie to be inserted for securing the arcuate members 112, 114 together in the latched position of the clamp 100.

The handle 124 of the first arcuate member 112 may extend generally radially outward from the terminal end of the first arcuate member 112 opposite the hinge assembly 116 and may be configured as a hand grip or a finger grip. For example, the handle 124 may be configured for a user to grasp with their hand or one or more fingers. As will be appreciated from FIG. 2, the bottom portion of the handle 124 may extend beyond the tie-receiving loop 122 to provide clearance for grasping the handle when a tie is joined to the tie-receiving loop 122. The base of the handle 124 joined to the first arcuate member 112 may be reinforced by one or more reinforcement ribs 125 or other reinforcement structure on the opposite side of the handle 124 from the tie-receiving loop 122.

Figure 4:
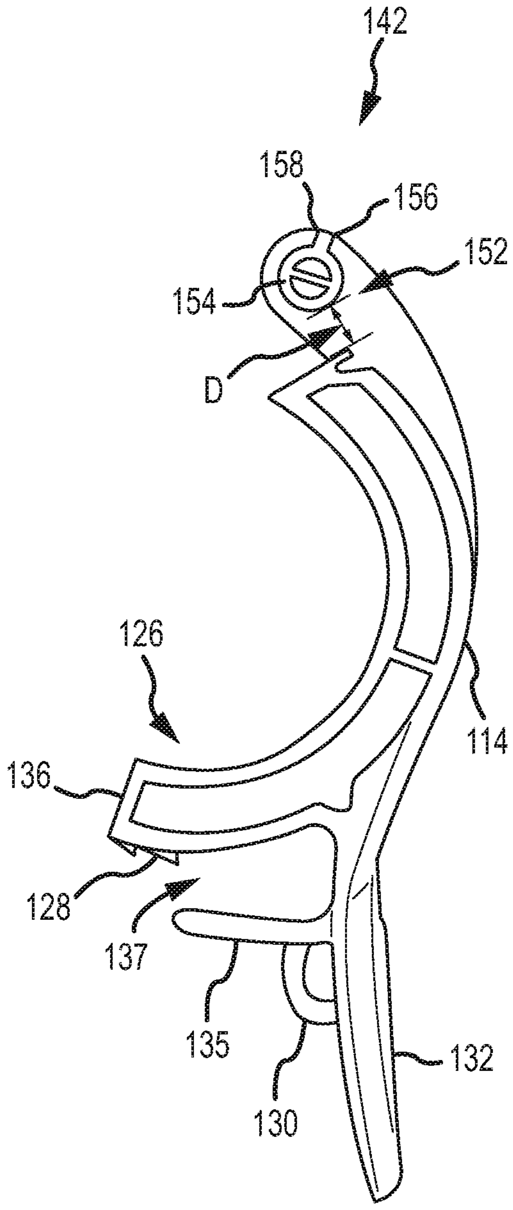
FIG. 4 is a side elevation view of another arcuate member of the claim of FIG. 1.

The second arcuate member 114 of the main body 110 may substantially form the other half of the clamp 100. As best shown in FIG. 4, an inner circumference of the second arcuate member 114 may form a semi-circular arc spanning about 180 degrees. At the end opposite the hinge assembly 116, the second arcuate member 114 may form the mating end 126 for receiving the latch finger 118 of the first arcuate member 112. The mating end 126 may be defined along the second arcuate member 114 for approximately the same length the latch finger 118 protrudes from the arc forming the first arcuate member 112.

An enclosure wall 135 may extend from the base of the handle 132 under the second tie-receiving loop 130, generally normal to the handle 132 and spaced apart from the outer surface of the second arcuate member 114 forming the mating end 126. A retention cavity 137 is formed between the enclosure wall 135 and the outer wall of the second arcuate member 114 along a portion of the mating end 126. The enclosure wall 135 may be provided to cover the free end of the latch finger 118 when the clamp 100 is in a closed position to protect it and prevent accidental release of the latch finger 118 from the mating end 126. For example, the enclosure wall 135 may prevent the latch finger 118 from moving radially outwardly and disengaging from the teeth 128 on the mating end 126.

The teeth 128 of the second arcuate member 114 may extend along an exterior surface of the mating end 126 of the second arcuate member 114. The teeth 128 may be arranged adjacent the terminal end of the mating end 126, i.e., the free end of the second arcuate member 114 when the clamp body 110 is assembled. The teeth 128 may be provided as one or a series of teeth that are configured to mesh or mate with the teeth 120 of the latch finger 118 of the first arcuate member 112. The opposing teeth 128 of the second arcuate member 114 may be formed on an outer wall of the second arcuate member 114 defining an outer diameter of the main body 110 of the clamp 100. The teeth 128 may also protrude as ridges or stepped barbs that taper downwardly toward the free end of the second arcuate member 114 opposite the hinge portion 116. A second tie-receiving loop 130 may be arranged on a wall of the handle 132 facing the first arcuate member 112. The second tie-receiving loop 130 may define an opening that enables one end of a zip-tie to be inserted. By inserting a zip tie through each of the first and second tie-receiving loops 122, 130, and securing or locking the zip-tie together, the clamp 100 may be secured in the closed, latched position of FIG. 2 to prevent accidental release of the clamp 100.

The handle 132 may extend at an angle outward from the second arcuate member 114 generally from an intermediate position along the second arcuate position 114 defining the beginning of the mating end portion 126. The handle 132 may be configured as a hand grip or as a finger grip. For example, the handle 124 may be configured for a user to grasp the handle with their hand or one or more fingers. As will be appreciated from FIG. 2, the bottom portion of the handle 132 may extend beyond the tie-receiving loop 130 and may provide clearance for grasping the handle when a tie is in place. The base of the handle 132 joined to the second arcuate member 114 may be reinforced by one or more reinforcement ribs 133 or other reinforcement structure.

In other implementations, enclosure walls may be provided on both arcuate members 112, 114 and may prevent accidental release of the toothed engagement between the finger latch 118 and the mating end 126. For example, enclosure walls may extend from both of the handles 124 and 132 and may contact each other in the closed, latched position of the clamp 100 to prevent access to the latch finger 118 from between the handles 124, 132. Enclosure walls may be provided in addition or as an alternative to first and second tie-receiving loops 122, 130 provided on the clamp 100.

Figure 2:
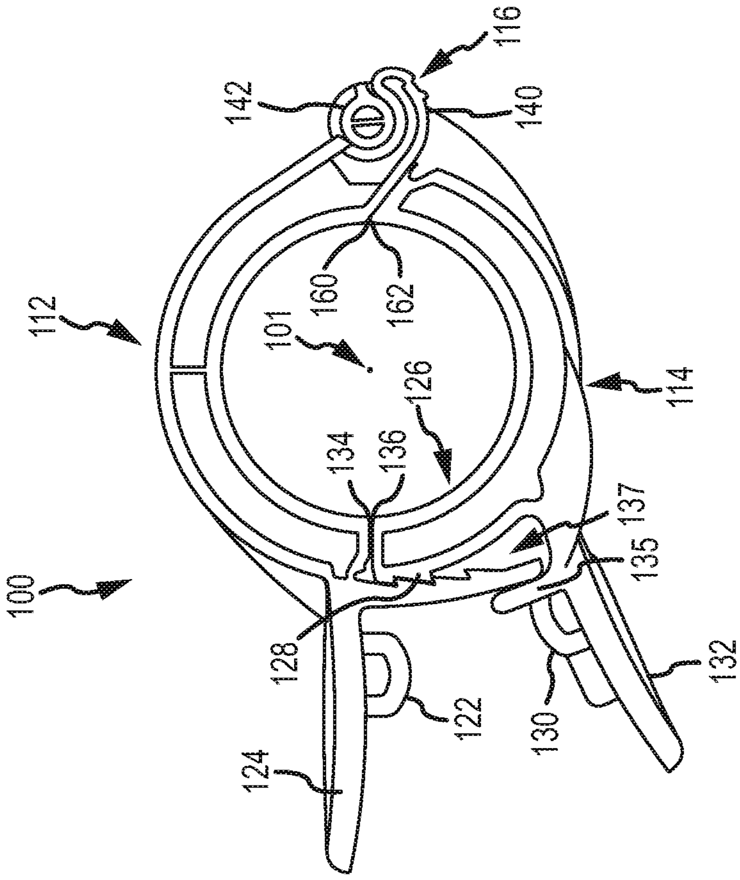
FIG. 2 is a side elevation view of the clamp of FIG. 1 in a closed position.

The handles 124, 132 may extend from their respective arcuate members 112, 114, and in the latched position of the clamp 100 as shown in FIG. 2, the handles 124, 132 may be slightly angled away from each other, approaching approximately parallel. The handles 124, 132 may be offset from each other by approximately 45 degrees with respect to the external circumference of the clamp body 110. arcuate member Turning to FIG. 2, the arcuate members 112, 114 may be clamped together in a closed, latched position, and a stop face 134 of the first arcuate member 112 may contact a stop face 136 of the second arcuate member 114. As the arcuate members 112, 114 move towards each other from the open position of FIG. 1 to the closed, latched position of FIG. 2, the teeth 120, 128 may slide along and past each other until the abutting engagement between the stop faces 134, 136 is established, which may correspond to the most proximal tooth of the teeth 120 of the latch finger 118 meshing with a most distal tooth of the teeth 128 of the mating end 126. As discussed further below, due to the stop faces 134, 136 contacting each other in the latched position, only slight clearance may be provided between the first and the second arcuate members 112, 114. Because the latch finger 118 of the clamp 100 may be exposed at least at the sides of the clamp 100 in the closed, latched position of FIG. 2, the clamp 100 may also be referred to as an external latched clamp.

Figure 24:
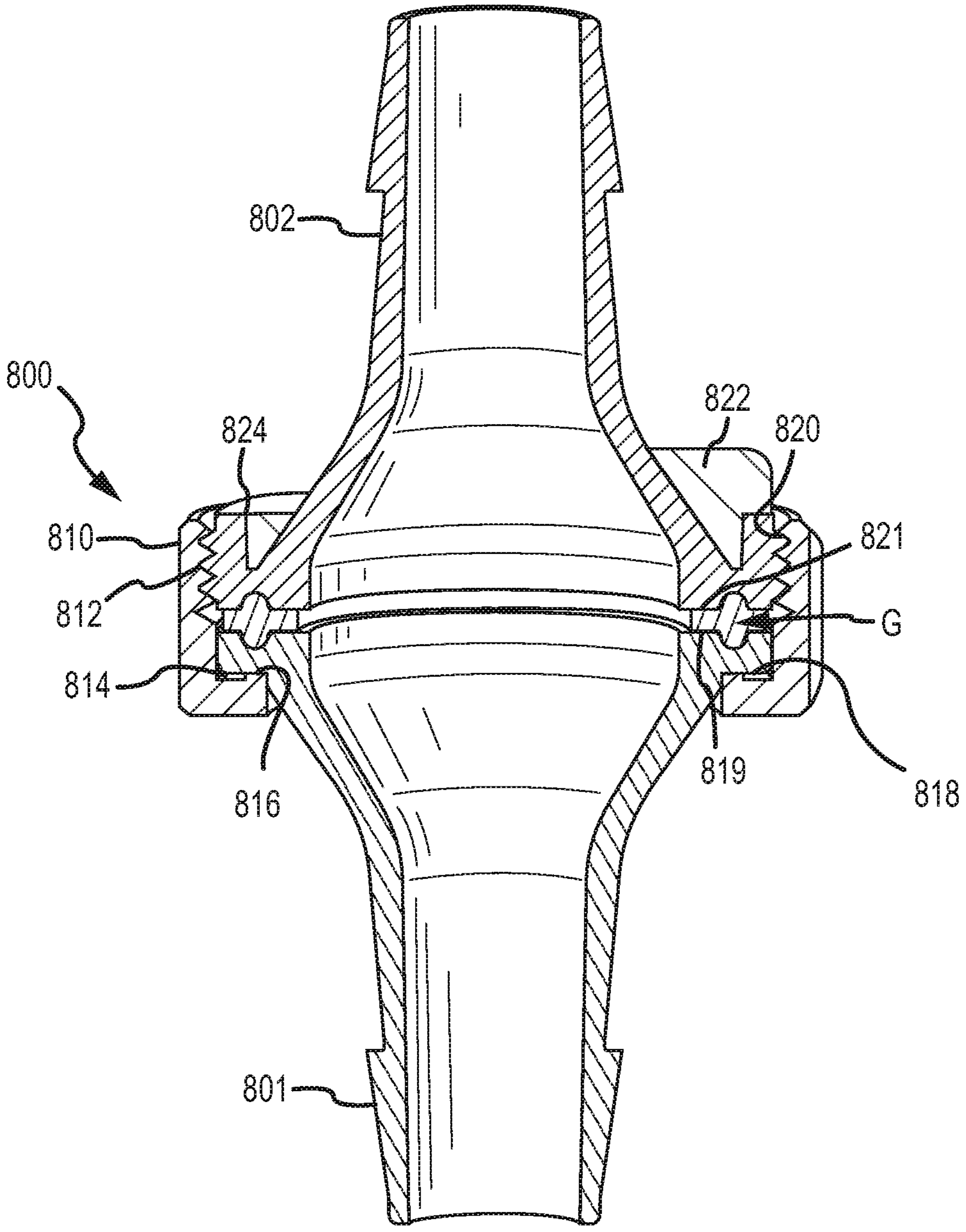
FIG. 24 is a cross-section view of the clamp, the sanitary fittings, and the gasket of FIG. 23.

The interior of the clamp body 110 may include a first channel 138 and a second channel 168 within an inner diameter wall of the first and second arcuate members 112, 114, respectively, for receiving the flange ends of a pair of sanitary fittings F (FIG. 7) and a washer or gasket G (FIG. 24). As illustrated in FIG. 1, the channels 138, 168 may be exposed in the open position of the clamp 100. The clamp 100 may open to a degree that enables the sanitary fittings F to be placed in the channel 138 of one of the arcuate members 112, 114. The arcuate members 112, 114 may be moved relative to each other by the hinge assembly 116 to move into the latched position of the clamp body 110 so that the portions of the channels 138, 168 defined by the arcuate members 112, 114 may engage the outer circumference of the sanitary fittings F. This may enable the sanitary fittings F to be nested and securely held within the interior of the clamp body 110 in the latched position of FIG. 2.

The hinge assembly 116 may enable the arcuate members 112, 114 to move relative to one another between the closed, latched position and the open position and may enable the arcuate members 112, 114 to be detached from one another. The hinge assembly 116 may include a barrel structure 140 formed on the first arcuate member 112 and a pin structure 142 formed on the second arcuate member 114. The barrel structure 140 and the pin structure 142 of the hinge assembly 116 may form the terminal ends of the arcuate members 112, 114, respectively. The barrel structure 140 may alternatively be formed on the second arcuate member 114 and that the pin structure 142 may alternatively be formed on the first arcuate member 112.

Figure 3:
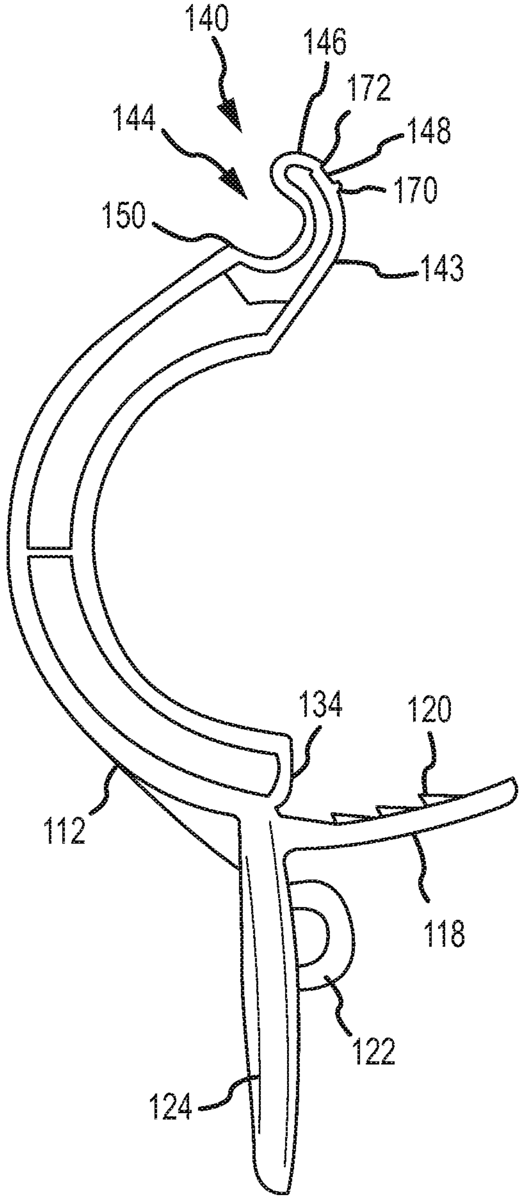
FIG. 3 is a side elevation view of an arcuate member of the clamp of FIG. 1.
Figure 5:
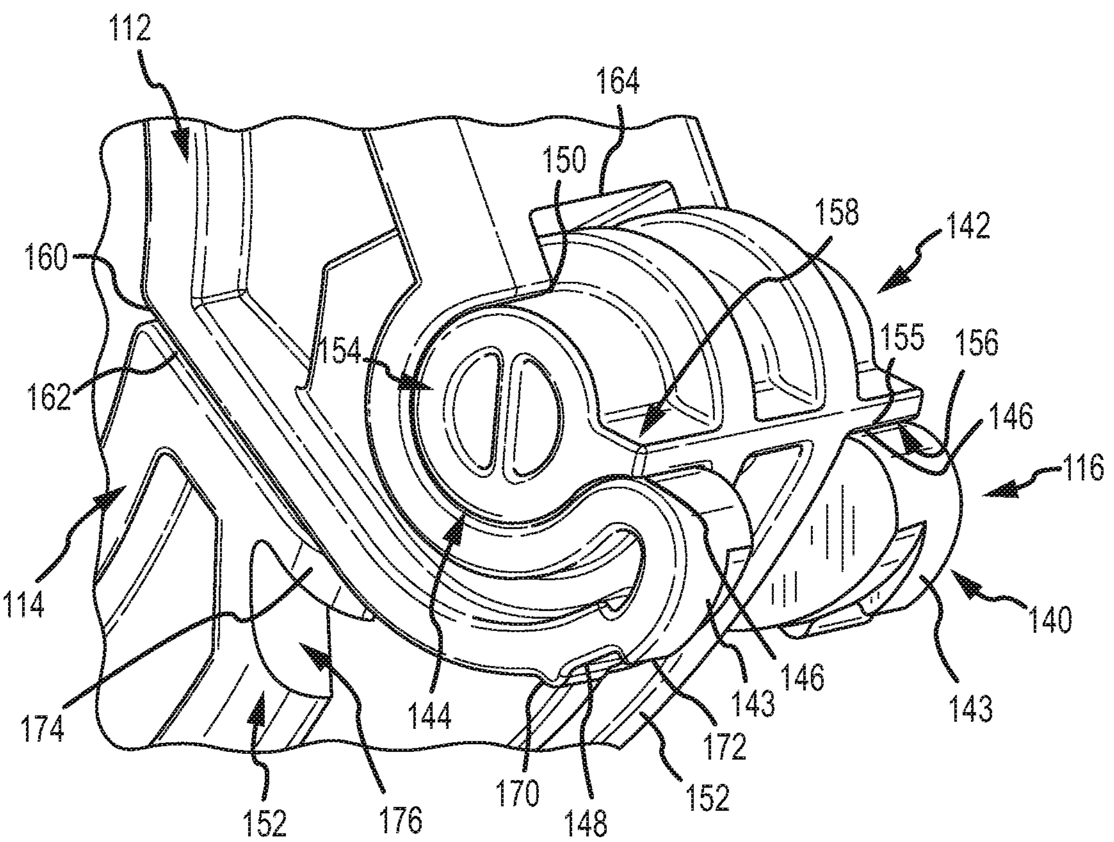
FIG. 5 is an enlarged view of the hinge of the clamp of FIG. 1 in the closed position.
Figure 6:
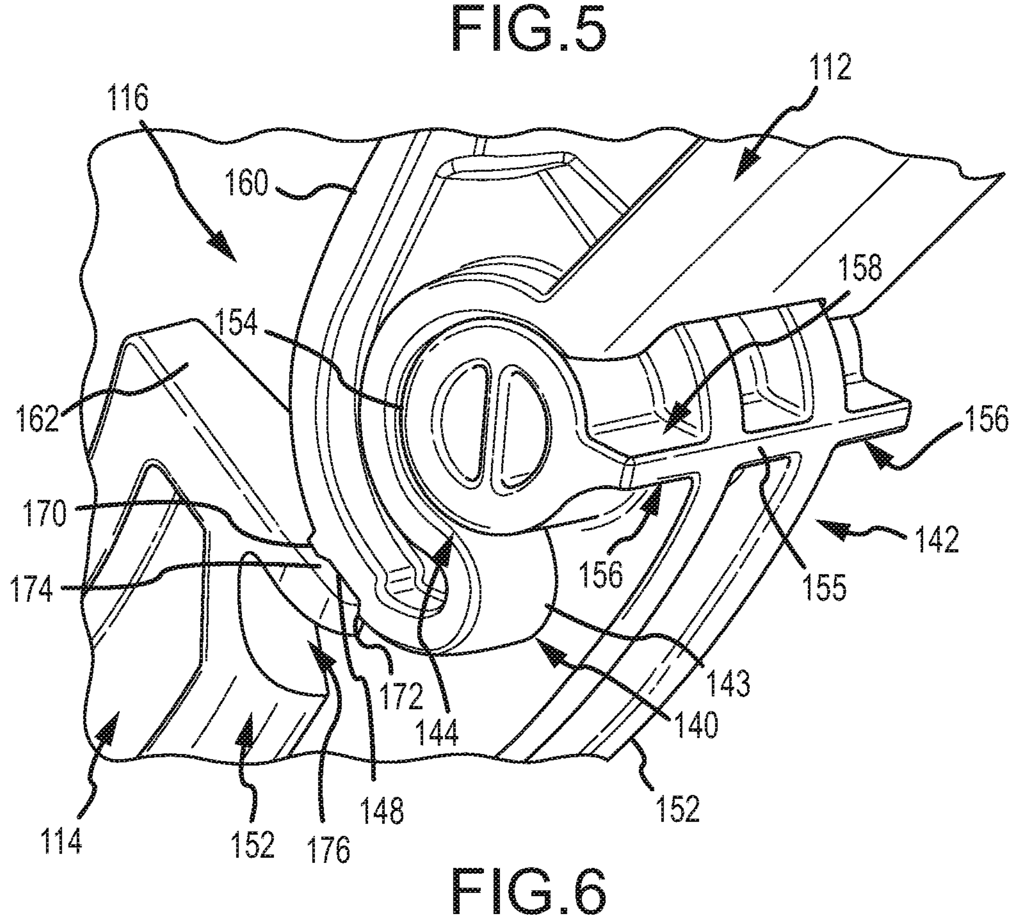
FIG. 6 is an enlarged view of the hinge of the clamp of FIG. 1 in the open position.

Turning to FIGS. 3 and 5-6, the barrel structure 140 of the hinge assembly 116 may be formed as two arcuate fingers 143 that may be received by the pin structure 142 of the hinge assembly 116 provided by the second arcuate member 114, as further described below. The arcuate fingers 143 may extend from the first arcuate member 112 in an arcing direction opposite the arcuate direction of the first arcuate member 112. The first arcuate member 112 in combination with the arcuate fingers 143 of the structure portion 140 may form an "S"-like shape.

Each arcuate finger 143 of the barrel structure 140 of the portion of the hinge assembly 116 provided by the first arcuate member 112 may define an pin-receiving recess 144, a first rotational stop 146, a second rotational stop 150, a biasing ridge 170, and a stop ridge 172. The pin-receiving recess 144 may be formed as a partially cylindrical recess with an open wall that faces outwardly, i.e., away from the second arcuate member 114 in the assembled state of the clamp body 110. The tip of each arcuate finger 143 may be rounded and function as a first rotational stop 146. The first rotational stops 146 may abut with the pin structure 142 of the second arcuate member 114 in the latched position, as further discussed below. The biasing ridge 170 may be formed as a bump on a ridge extending laterally across a width of the outer curved surface of each of the arcuate fingers 143 opposite the pin-receiving recess 144. The stop ridge 172 may also be formed as a bump, ridge, or wall extending laterally across a width of the outer curved surface of each of the arcuate fingers 143. The biasing ridge 170 and the stop ridge 172 may be spaced apart from each other along the arcuate fingers 143 with the stop ridge 172 positioned adjacent the first rotational stop 146 at the tip. A holding recess 148 may be defined as the space between the biasing ridge 170 and the stop ridge 172. In the open position of the clamp body 110 depicted in FIGS. 1 and 6, the combination of the biasing ridge 170 and the stop ridge 170 may hold the arcuate members 112, 114 open relative to one another by engaging with a surface of the second arcuate member 114 as further described below. In some implementations, a second rotational stop 150 of the first arcuate member 112 may be defined at a proximal end of the pin-receiving recess 144 opposite the first rotational stop 146 and may abut a ridge face 158 of the pin structure 142 of the second arcuate member 114 when the arcuate members 112, 114 are in an open position as further described below. The second rotational stop 150 may merely be the terminal end of the outer surface of the clamp portion 110 of the arcuate member 112 adjacent the pin-receiving recess 144.

Turning to FIGS. 4-6, the pin structure 142 of the hinge assembly 116 provided by the second arcuate member 114 may include a supporting hinge flange 152 extending from the end of the second arcuate member 114 opposite the handle 132. The hinge flange 152 may provide structural rigidity to the second arcuate member 114 and may provide structures and surfaces for guiding movement of the second arcuate member 114 with respect to the first arcuate member 112. The hinge flange 152 may be configured to support a pair of axles or posts 154. In an assembled clamp 100, the arcuate fingers 143 of the first arcuate member 112 may flank the hinge flange 152 and couple with the posts 154 of the second arcuate member 114. The hinge flange 152 may extend generally tangentially from the outer circumference of the second arcuate member 114.

The pair of posts 154 of the pin structure 142 of the hinge assembly 116 provided by the second arcuate member 114 may extend laterally from each side of the hinge flange 152, and the posts 154 may be arranged parallel to the central axis 101 (see FIG. 2) of the clamp 100. The posts 154 of the pin structure 142 may be configured to be received within and cradled by the pin-receiving recess 144 of the first arcuate member 112 to function together as a pin for the hinge assembly 116. Each post 154 may have an outer diameter that may be approximately the same as an inner diameter of the pin-receiving recesses 144 of first arcuate member 112, and the surfaces of the pin-receiving recesses 144 may cradle and rotate about the outer surfaces of the posts 154 upon relative movement of the first and second arcuate members 112, 114.

The pair of posts 154 disposed on the hinge flange 152 of the second arcuate member 114 may be spaced at a distance D (FIG. 4) from the terminal end of the second arcuate member 114. The distance D may correspond to a width of the arcuate fingers 143 of the barrel structure 140 of the first arcuate member 112, which may enable the arcuate fingers 143 to be placed along opposing surfaces of the hinge flange 152 and inserted between the terminal end of the second arcuate member 114 and the posts 154. The hinge flange 152 may provide a support surface for the arcuate fingers 143, for example, as the first and second arcuate members 112, 114 rotate relative to one another.

Each post 154 of the hinge assembly 116 provided on the second arcuate member 114 may define a stop ridge 155 with a first face ridge 156 and a second ridge face 158 extending radially from the posts 154. Each stop face 156, 158 may be configured for limiting relative rotation between the first and second arcuate members 112, 114. For example, the first ridge face 156 of the second arcuate member 114 may abut the first rotational stop 146 of the first arcuate member 112 in the latched position of the clamp body 110 (FIG. 5), and the second ridge face 158 of the second arcuate member 114 may abut the second rotational stop 150 of the first arcuate member 112 in an open position of the clamp body 110 (FIG. 6). The stop ridge 155 may be formed as a single structure as shown in FIGS. 5 and 6, extending from each of the posts 154 and from the hinge flange 152 in between. Alternatively, the ridge stop 155 may be formed as two separate structures extending independently from each of the posts 154.

While the barrel structure 140 may be formed on the first arcuate member 112 and the pin structure 142 may be formed on the hinge flange 152 extending from the second arcuate member 114, it may be understood that the barrel structure 140 and the pin structure 142 may be provided on either of the first and second arcuate members 112, 114.

With specific reference to FIG. 5, the hinge assembly 116 is shown when the clamp 100 is in a latched position. In this position, the first rotational stop 146 of the barrel structure 140 of the first arcuate member 112 may abut the first stop face 156 of the pin structure 142 of the second arcuate member 114. In the latched position, the first and the second stop faces 134, 136 (see FIG. 2) and the third and fourth stop faces 160, 162 may additionally respectively abut each other. A guide recess 164 may be formed in an end surface of the first arcuate member 112 between the arcuate fingers 143 to provide clearance for the back edge of the hinge flange 152. The interface between the guide recess 164 and the hinge flange 152 may provide additional support for the hinge assembly 116.

In the closed, latched position of the clamp 100, abutting contact between opposing stop faces 134, 136 and 160, 162, of the first and second arcuate members 112, 114, may provide only a slight gap, if any, between the two portions of the clamp body 110. The first and the second stop faces 134, 136 of the arcuate members 112, 114 may be formed at complementary angles, thereby providing abutting contact in the closed position. Similarly, the third and the fourth stop faces 160, 162 of the arcuate members 112, 114 may be formed at complementary angles relative to each other to provide abutting contact. It may be appreciated from FIG. 2 that the complementary angles of the first and second stop faces 134, 136 of arcuate members 112, 114 may differ from the complementary angles of the third and fourth stop faces 160, 162 of the arcuate members 112, 114. The abutting stop faces 134, 136 and 160, 162 may enable the clamp 100 to provide a 360 degree seal for exerting equal sealing pressure around the circumference of the sanitary fitting(s) and gasket arranged within the clamp 100. The abutting contact between the first rotational stop 146 of the first arcuate member 112 and the first stop face 156 of the second arcuate member 114 may prevent additional rotation or over-rotation of the arcuate members 112, 114, which may prevent overstressing of the clamp 100 at the stop faces 134, 136 and 160, 162. This arrangement may also help avoid over-compression of components held in a circular seal within the clamp 100 and may reduce the possibility of failure of the seal between the clamped components.

Figure 8:
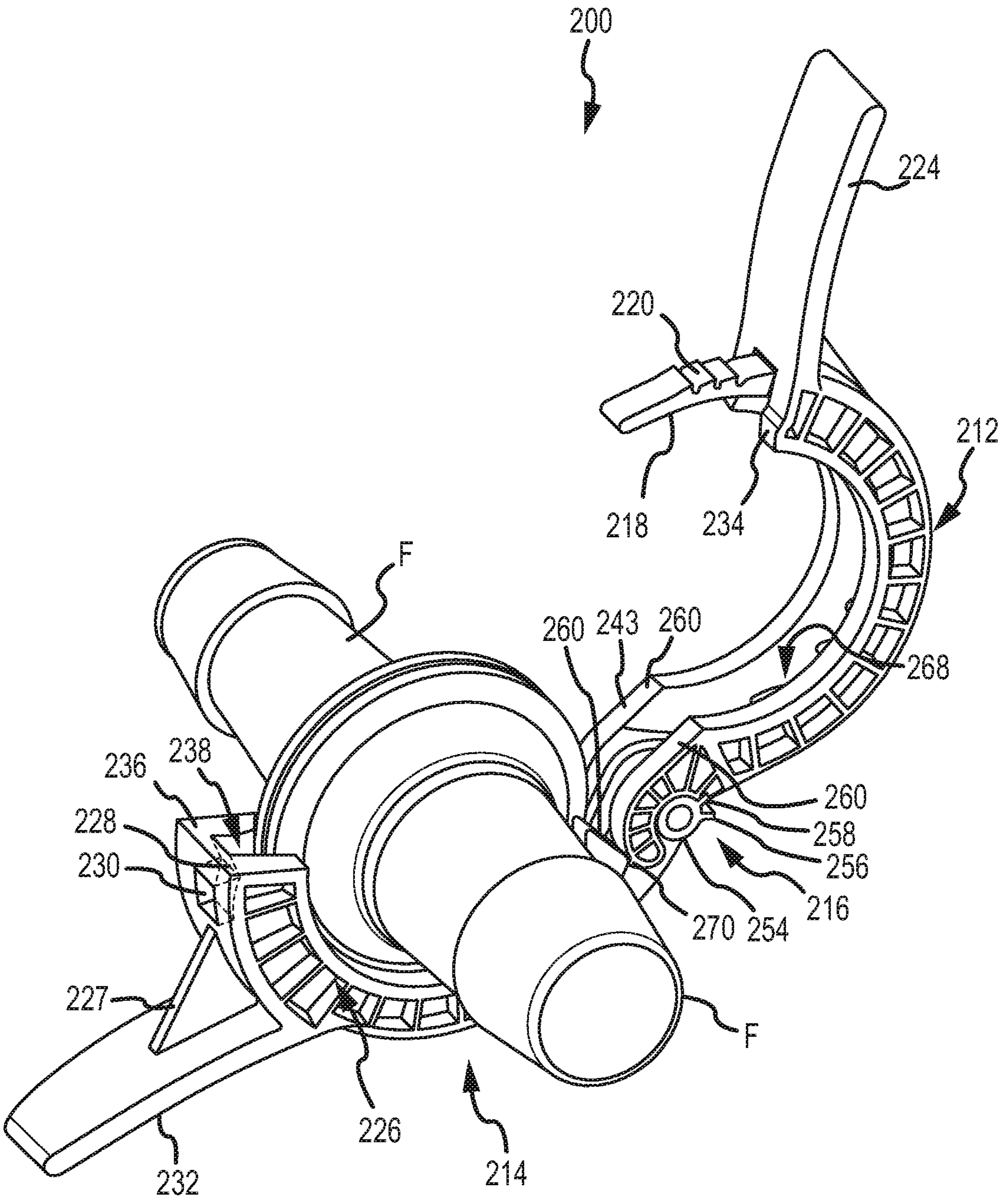
FIG. 8 is a front isometric view of another implementation of a clamp in an open position.

An enlarged section view of the clamp 100 with the hinge assembly 116 in the open position is illustrated in FIG. 6. The hinge assembly 116 may be held in the open position by the biasing ridge 170 on the arcuate fingers 143 engaging with the surface of the fourth stop face 162 of the second arcuate member 114 in a friction fit. The holding recess 148 flanked by the biasing ridge 170 and the locking ridge 172 may provide clearance for the locking ridge 172 to interface with a lip extension 174 of the second arcuate member 114 while the biasing ridge 170 holds the clamp 100 open in a friction fit with the stop face 162. Upon assembly of the first and second arcuate members 112, 114 together, when the locking ridge 172 moves in a counterclockwise direction (per the orientation of FIGS. 5 and 6) past the lip extension 174, the first arcuate member 112 is locked into a hinge pivot relationship with respect to the second arcuate member 114 that will not disconnect unless substantial force is applied to move the locking ridge 172 past the lip extension 154 in a clockwise direction (per the orientation of FIGS. 5 and 6.) This position, as shown in FIG. 8 defines the widest opening of the clamp 100 in an open position. This may be the initial configuration of the clamp 100 when shipped to a user. The locking ridge 172 will not move past the lip extension 154 onto the stop face 162 unless substantial force is applied to move the locking ridge 172 past the boundary edge 176 in a clockwise direction (per the orientation of FIGS. 5 and 6). This may be done if it is desired to separate the first and second arcuate members 112, 114 from each other.

The holding recess 148, the biasing ridge 170, and the locking ridge 172 of the first arcuate member 112 may extend across all or a portion of the width of the arcuate fingers 143 of the first arcuate member 112. The biasing ridge 170 and the locking ridge 172 may be formed as protrusions on either side of the holding recess 148, or the holding recess 148 may be formed as a recess in the wall of the arcuate fingers 143.

The second arcuate member 114 with the lip extension 174 may form an undercut 176 defined below the lip extension 174. The lip extension 174 and the undercut 176 may be defined in the diameter of the second arcuate member 114 outer, adjacent the stop face 162. The undercut 176 may enable some movement or flexion of the lip extension 174 towards the undercut 176 to aid in passage of the locking ridge 172 off and on the stop face 162 and provide a spring-type bias against the biasing ridge 170.

In operation of the clamp body 110, when the first arcuate member 112 is separate from the second arcuate member 114, the clamp body 110 may be assembled by inserting the arcuate fingers 143 of the barrel structure 140 of the first arcuate member 112 into the area between the posts 154 of the pin structure 142 and the terminal end of the second arcuate member 114 defining the stop face 162. The arcuate fingers 143 may slide along the sidewall surfaces of the hinge flange 152 until the locking ridge 172 moves between the post 154 and stop face 162 past the free end of the lip extension 174. Movement of the locking ridge 172 along the lip extension 174 may cause the lip extension 174 to flex into the undercut 176, thereby enabling the locking ridge 172 to move past the distal end of the lip extension 174.

Pivoting movement between the first and second arcuate members may be guided by the pin-receiving recess 144 rotating about the posts 154. In the open position of the clamp 100, the arcuate members 112, 114 of the clamp 100 at their respective handle ends opposite the hinge assembly 116 may be spaced by a maximum distance apart. This may facilitate insertion of one or more components such as sanitary fittings into the channel 138, while at the same time, the arcuate members 112, 114 being held in the locked-in position may prevent the arcuate members 112, 114 from moving during such an operation. According to certain implementations, a maximum angular distance the arcuate members 112, 114 may rotate apart and together may correspond to an angular distance between the first ridge face 156 and the first rotational stop 146 when the arcuate members 112, 114 are in an open position. This distance may be approximately between 90 and 120 degrees.

In order to move the arcuate members 112, 114 from the open position of the clamp 100 into a closed, locked position, a user may exert a force on the first arcuate member 112 and the second arcuate member 114 to move the biasing ridge 170 off of the of the lip extension 174 of the stop face 162. Movement of the biasing ridge 170 against and along the lip extension 174 may be guided by the post-receiving recess 144 of the first arcuate member 112 rotating about the post 154 of the second arcuate member 114. The post 154 may serve as a fulcrum for the first arcuate member 112 and provide leverage to slide the biasing ridge 170 along the stop face 162 and apply pressure on the lip extension 172 to deflect the lip extension 172 into the undercut 176.

Figure 7:
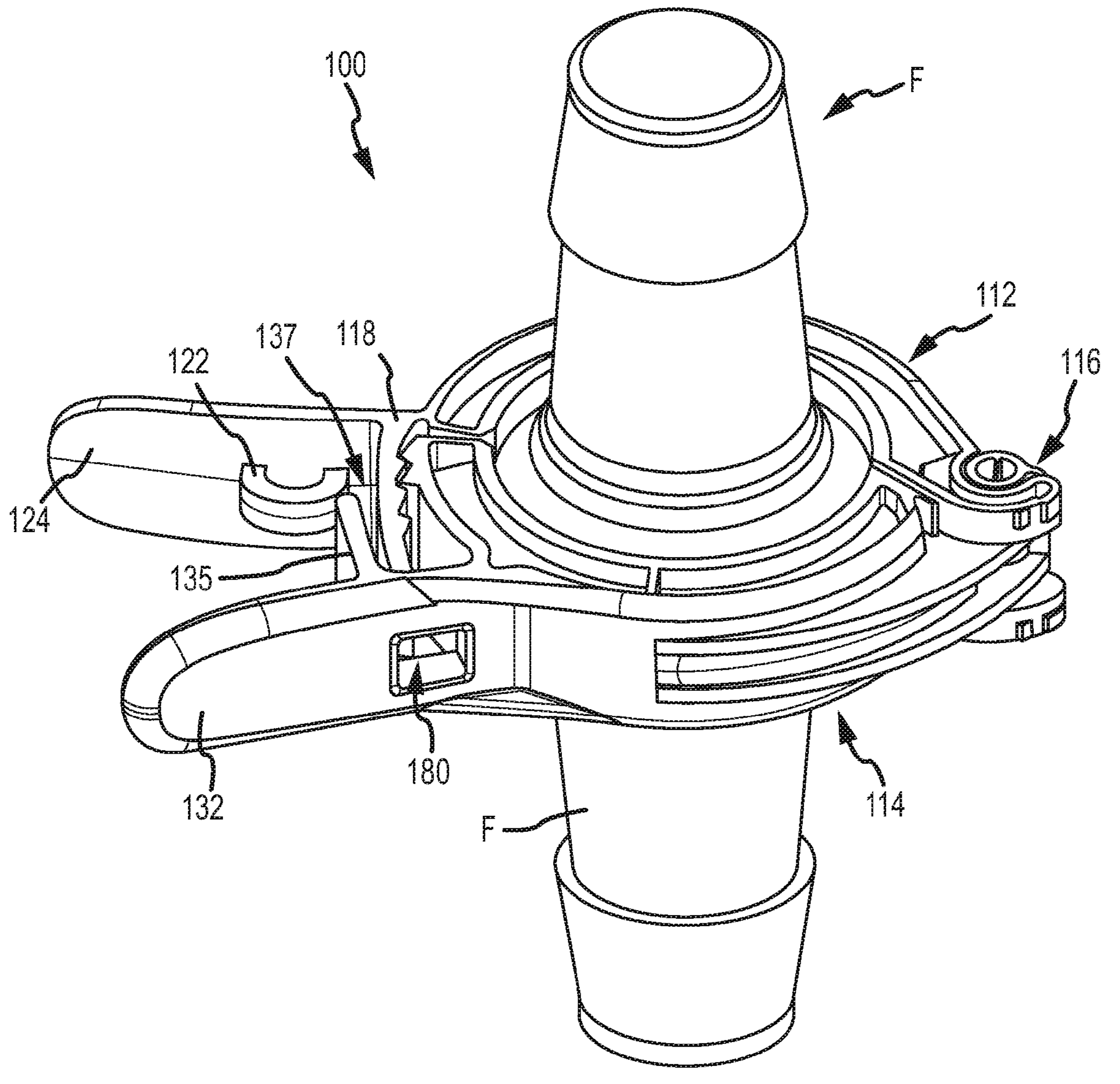
FIG. 7 is a bottom isometric view of the clamp of FIG. 1 in the latched position with a sanitary fitting arranged therein.

After overcoming the bias resistance to move the arcuate members 112, 114 towards one another, the clamp body 110 may closely engage with the components nested in the channels 138, 168, e.g., the circular flanges of the sanitary fittings F (see FIG. 7). Continued movement in this direction may cause the latch finger 118 to be inserted into the retention cavity 137 on the mating end 126 of the second arcuate member 114. The teeth 120 of the latch finger 118 may progressively engage and disengage with the teeth 128 of the mating end 126 until the latched position of FIG. 2 is reached, in which the stop faces 134, 160 of the first arcuate member 112 abut with the stop faces 136, 162 of the second arcuate member 114.

Movement of the arcuate members 112, 114 to the latched position may be enabled by a user grasping and forcing the handles 124, 132 towards one another. In addition or alternatively, the external surface of the arcuate members 112, 114 may be forced together by hand or by pliers, for example. A zip-tie, twist tie, wire, cord or other connecting device (not shown) may be inserted into the loops 122, 130 for securing or locking the clamp body 110 in the latched position. Upon securing the clamp 100 in the latched position, the one or more sanitary fittings engaged within the channels 138, 168 may be used for the sterile transfer of contents from one receptacle to another. The configuration of the clamp 100 with the stop faces 134, 160 abutting the stop faces 136, 162 may provide a circular closure so that the side walls 139, 141 exert a 360 degree equal sealing pressure around the entire circumference of the sanitary fittings.

Channels 138, 168 may be configured to receive multiple components, such as two sanitary fittings and one or more gaskets. The sidewalls 139, 141 defining the channels 138, 168 may be formed at an angle with respect to the radius of the clamp 100 to provide a wide opening for the channels 138, 168 that narrows with depth. The angled sidewalls 139, 141 of the channels 138, 168 facilitate clamping the sanitary fittings and gasket together and crating a seal. Upon moving the clamp 100 to the closed, latched position the angled sidewalls 139, 141 slowly compress the flanges of the sanitary fittings F together with the gasket G in between as the distance between the sidewalls 139, 141 decreases when the flanges of the fittings F extend more deeply into the channels 139, 141. However, the diameter of the clamp 100 in the closed position and the graduated width of the channels 139, 141 are designed with respect to the diameter of the flanges on the fittings F and the combined thickness of the flanges and the gasket G to ensure that the flanges and gasket G are not over-compressed when the clamp 100 is in its closed, latched position.

Alternatively, from the open position of the clamp 100 (FIGS. 1 and 6), the user may separate or detach the arcuate members 112, 114 from each other by rotating the latching ends of the first and second arcuate members 112, 114 away from each other. Movement of the locking ridge 172 past a distal end of the lip extension 174 towards the proximal end of the stop face 162 may be guided by the pin-receiving recess 144 rotating about the post 154. The posts 154 may serve as a fulcrum for the first arcuate member 112 to force the locking ridge 172 onto the lip extension 174 by deflecting the lip extension 174 into the undercut 176 so that the locking ridge 172 may move towards the central axis 101 of the clamp 100. As the arcuate members 112, 114 are rotated apart from one another, the second rotational stop 150 of the first arcuate member 112 may abut the second ridge face 158 of the second arcuate member 114. This enables the user to exert a force between the arcuate members 112, 114 about the hinge assembly at the point of abutting contact to extract the arcuate fingers 143 from between the posts 154 and the respective third and fourth stop faces 160, 162.

From the open position of the clamp 100, the forces used to move the clamp 100 in and out of the open position may be based, in part, on the size and shape of the biasing ridge and the locking ridge 172, on the degree of movement of the terminal lip 174 into the undercut 176, and on the forces exerted between the posts 154 of the pin structure 142 and the pin-receiving recess 144 of the barrel portion 140.

According to some implementations, the clamp body 110 may be configured so that unlocking the arcuate members 112, 114 requires a large degree of force to be exerted to move the latch finger 118 relative to the mating end 126. In such implementations, the clamp 100 may be configured for a single-use or for limited use. In other implementations, the clamp body 110 may also be unlatched from the latched position of FIG. 2. The latch finger 118 may be detached from the mating end 126 by forcing the finger latch 118 outwardly and away from the teeth 128 on the mature receiving end 126 so that the arcuate members 112, 114 may be pulled apart. In some implementations, in order to release the latched engagement between the teeth 120 of the latch finger 118 and the teeth 128 of the mating end 126 in the closed, latched position of the clamp 100, a user may slide a tool such as a screwdriver through a latch release window 180 (see FIG. 7) defined by walls extending through the handle 132 from the bottom surface to the top surface. The tool may be used to force the latch finger 118 radially outwardly from the mating end 126 so that the engaged teeth 120, 128 are forced apart from each other. The user may then pull the handles 124 and 132 away from each other in order to open the latch 100.

FIGS. 8-11 illustrate an exemplary implementation of another clamp 200 with an internal latch. The clamp 200 may differ from the clamp 100 described above in connection with FIGS. 1-7 by the internal latch configuration in which the latch finger 218 of the first arcuate member 212 of the clamp 200 is received within an interior of a mating sleeve 226 of the second arcuate member 214. In addition, the clamp 200 may include a hinge assembly 216 that differs from the hinge assembly 116 of the clamp 100. The clamp 200 may be similar structurally and functionally to the clamp 100 in other respects and, for example, may include handles 224, 232. Accordingly, in operation of the clamp 200, the first arcuate member 212 (see FIG. 9) and the second arcuate member 214 (see FIG. 10) may be detachable from one another, and the clamp 200 may assume a closed, latched position as in FIG. 11.

The finger latch 218 of the first arcuate member 212 of the clamp 200 may include radially outward-facing teeth 220 and the mating sleeve 226 of the second arcuate member 214 may include radially inward-facing teeth 228 (see cutaway of FIG. 10) disposed on the outer diameter interior wall of the mating sleeve 226. The teeth 220, 228 may form a toothed engagement in a similar manner as described above in connection with the clamp 100 of FIGS. 1-7 when the clamp 200 is in a closed position.

Figure 11:
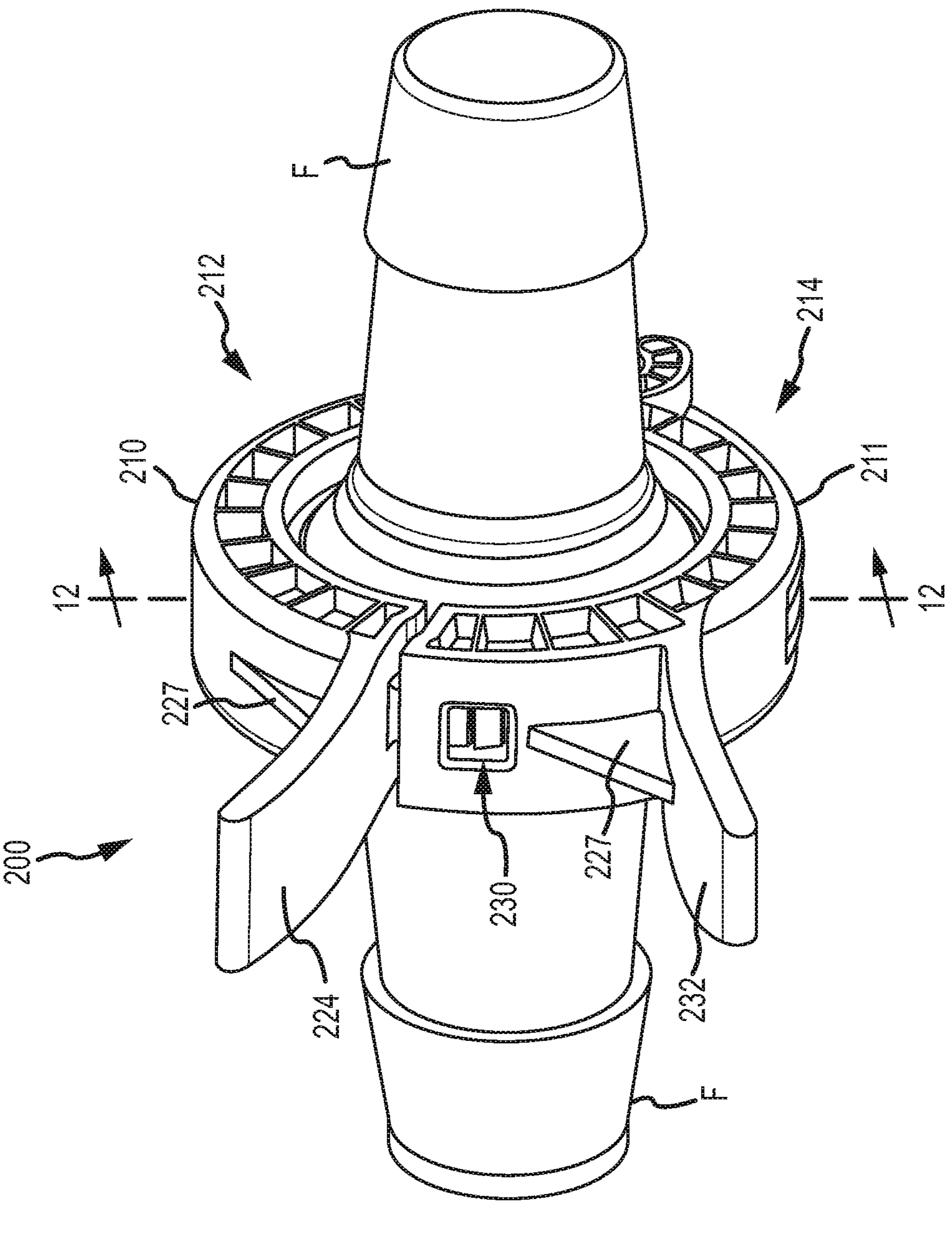
FIG. 11 is a front isometric view of the clamp of FIG. 8 holding a sanitary fitting in the closed position.

From the latched position of the clamp 200 illustrated in FIG. 11, the internal latch engagement between the teeth 220 and 228 of the clamp 200 may be released by inserting a rigid tool into a latch release window 230 formed through the outer wall of the mating sleeve 226. The rigid tool may be pushed through the latch release opening 230 into an interior of the mating sleeve 226 to move the latch finger 218 radially inwardly until the teeth 220 of the latch finger 218 are released from the teeth 228 of the mating sleeve 226. The first and second arcuate members 212, 214 may then be moved apart by pulling the handles 124, 132 away from each other.

Figure 9:
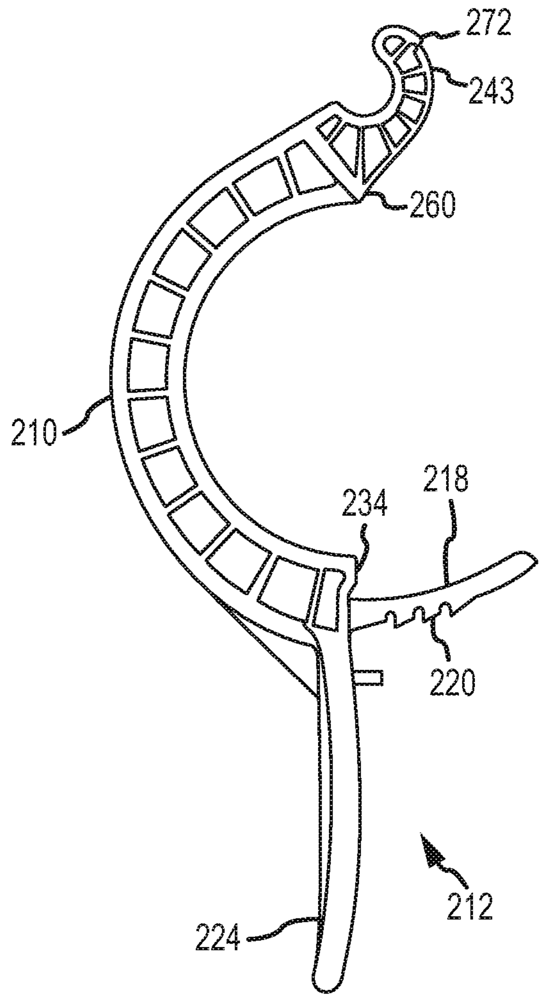
FIG. 9 is a side elevation view of an arcuate member of the clamp of FIG. 8.
Figure 10:
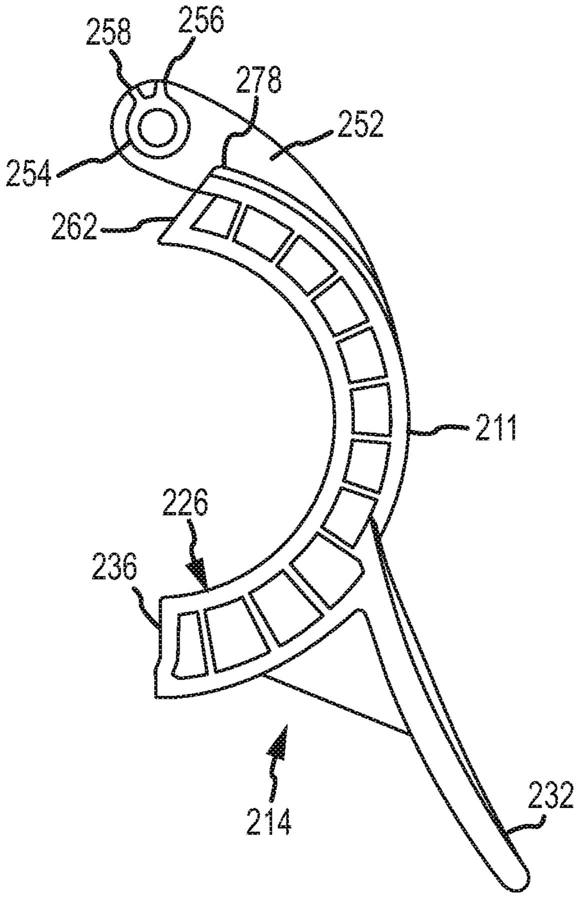
FIG. 10 is a side elevation view of another arcuate member of the clamp of FIG. 8.

The hinge assembly 216 of the clamp 200 is similar to the hinge assembly of the previous embodiment. A locking ridge 272 may be formed on an outer edge of each of the arcuate fingers 243 as shown in FIG. 9. In this embodiment, however, there is no biasing ridge or lip flange on the second arcuate member 214. Upon assembly of the first and second arcuate members 212, 214 together, when the locking ridge 272 moves in a counterclockwise direction (per the orientation of FIGS. 8-10) past a boundary edge 278 of the stop face 262, the first arcuate member 212 is locked in to a hinge pivot relationship with respect to the second arcuate member 214. Upon clockwise rotation of the first arcuate member 212 with respect to the second arcuate member 214 to open the clamp 200, the locking ridge 272 will catch on the boundary edge 278, preventing further movement of the first and second arcuate members 212, 214. This position, as shown in FIG. 8 defines the widest opening of the clamp 200 in an open position. The locking ridge 272 will not move past the boundary edge 278 onto the stop face 262 unless substantial force is applied to move the locking ridge 272 past the boundary edge 276 in a clockwise direction (per the orientation of FIG. 8). This may be done if it is desired to separate the first and second arcuate members 212, 214 from each other.

The clamp 200 may be provided with reinforcement members such as the reinforcement wall 227 extending between the mating sleeve 226 and the handle 232 of the second arcuate member 214. A reinforcement wall 227 may also be provided between the handle 224 and the first arcuate member 212 to provide additional support for the handle 224 when placed under stress.

Figure 12:
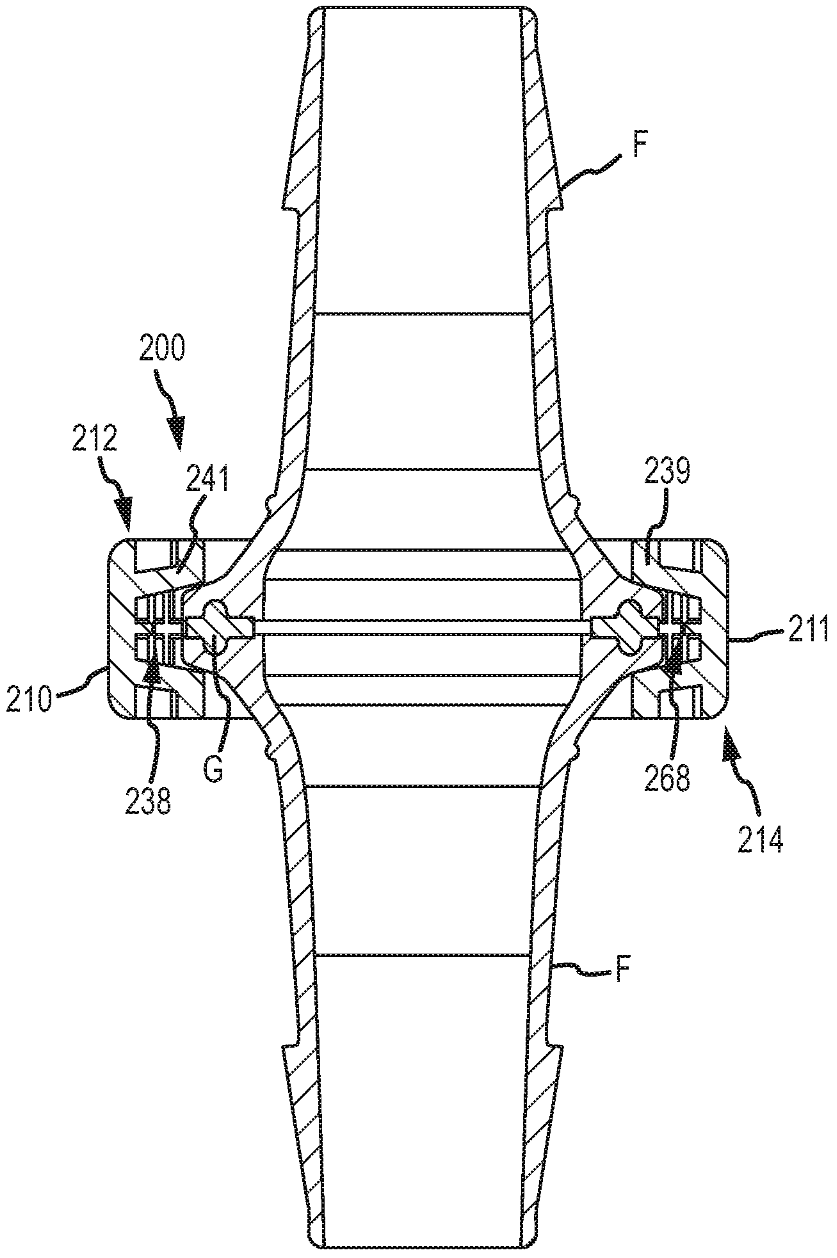
FIG. 12 is a cross-section view of the clamp of FIG. 8 as indicated by lines 12-12 in FIG. 11.
Figure 13:
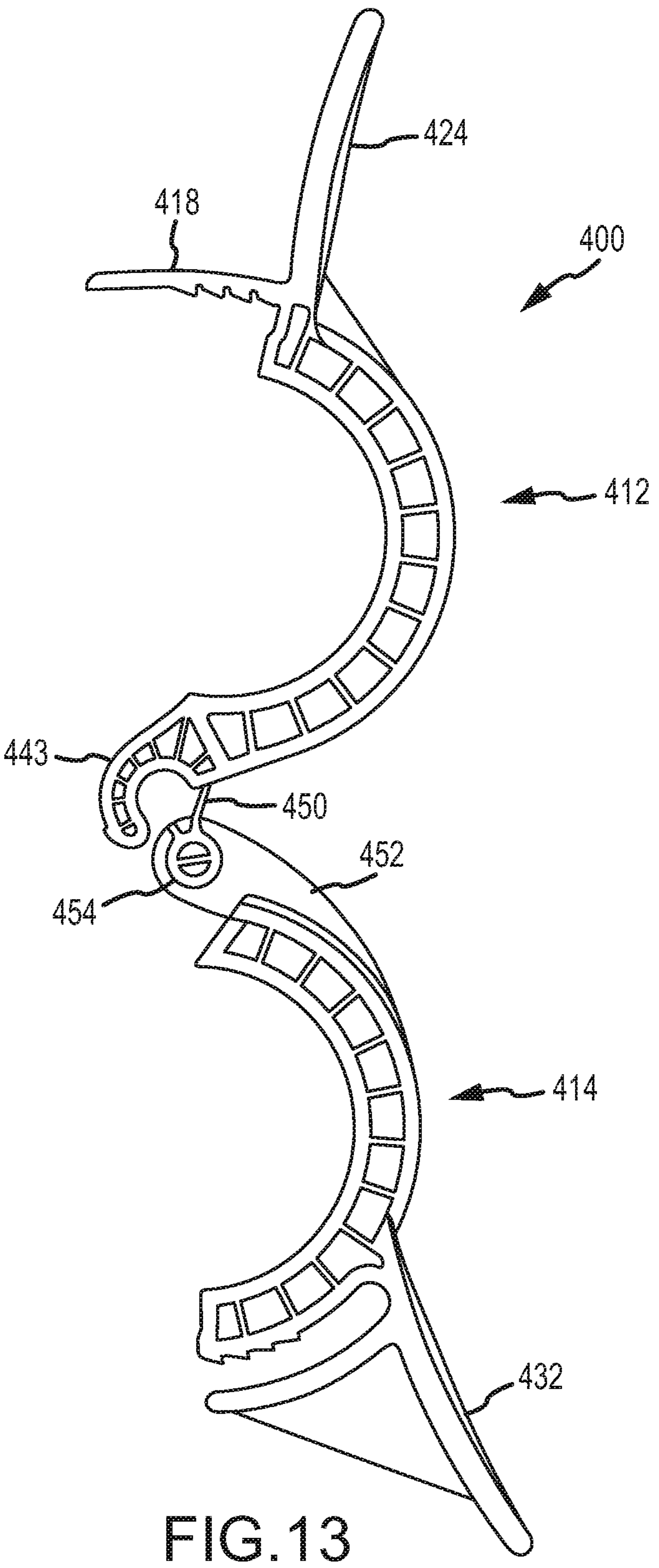
FIG. 13 is a side elevation view of another implementation of a clamp in an unassembled, tethered position.
Figure 14:
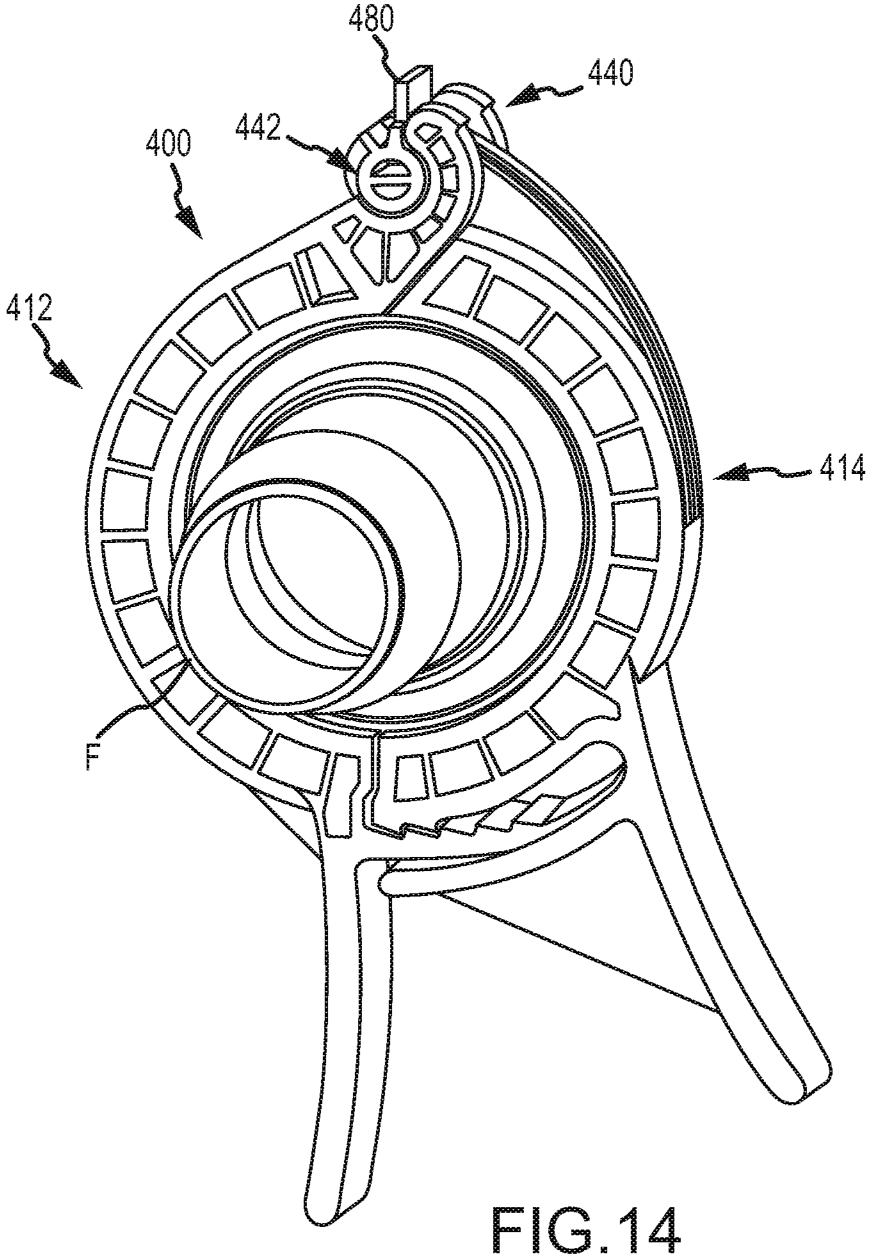
FIG. 14 is a side isometric view of the clamp of FIG. 13 in an assembled, closed position.

FIG. 12 illustrates a cross-section view of the clamp 200 in the closed, latched position. Any number of types of sanitary fittings and gaskets may be used in connection with the clamp 200, and the fittings may, for example, have a distal end with a hose barb (as shown), a flange configured for hermetically sealing with a bag of fluid or powder material used in a manufacturing process, a ring for stabilization and/or coupling with another clamp and/or fitting (not shown), or another configuration. Similar to the clamp 100, the clamp 200 may establish a circular closure around the sanitary fittings F and the gasket G contained within the channels 238, 268. The clamp 200 may be configured so that the channels 238, 268 are defined by walls 239, 241 that extend 360 degrees around the clamp 200, with deminimis interruptions only at the stop faces 234, 236 and 260, 262. However, due to the abutting contact between the stop faces 234 and 236 and between stop faces 260 and 262, the clamp 200 may provide equal sealing pressure to the sanitary fittings F and the gasket G arranged therein. Providing equal sealing pressure using the clamp 200 may prevent over-compression of the sanitary fittings F on the gasket G, thereby avoiding catastrophic failure to the connection due, for example, to the gasket G extruding outside of the sanitary fittings F from the over-compression.

Generally, the flange of the sanitary fittings F may have an external diameter slightly smaller than the internal diameter of the channels 238, 268 when the clamp 200 is in the closed position. Channels 238, 268 may be configured to receive multiple components, such as two sanitary fittings and one or more gaskets. The sidewalls 239, 241 defining the channels 238, 268 may be formed at an angle with respect to the radius of the clamp 200 to provide a wide opening for the channels 238, 268 that narrows with depth. The angled sidewalls 239, 241 of the channels 238, 268 facilitate clamping the sanitary fittings and gasket together and crating a seal. Upon moving the clamp 200 to the closed, latched position the angled sidewalls 239, 241 slowly compress the flanges of the sanitary fittings F together with the gasket G in between as the distance between the sidewalls 239, 241 decreases when the flanges of the fittings F extend more deeply into the channels 239, 241. However, the diameter of the clamp 200 in the closed position and the graduated width of the channels 239, 241 are designed with respect to the diameter of the flanges on the fittings F and the combined thickness of the flanges and the gasket G to ensure that the flanges and gasket G are not over-compressed when the clamp 200 is in its closed, latched position.

Figure 15:
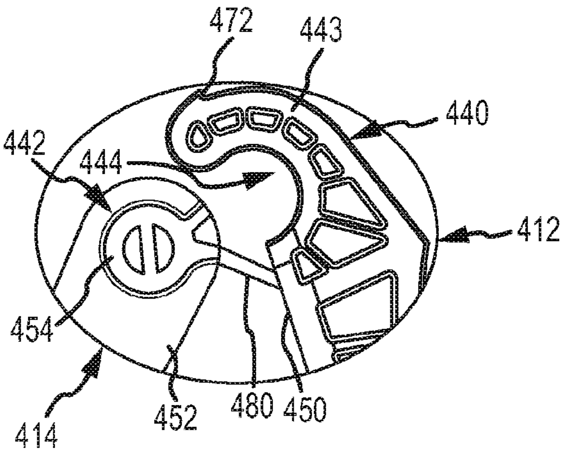
FIG. 15 is an enlarged view of the hinge of the clamp of FIG. 13 in the tethered, unassembled position.
Figure 16:
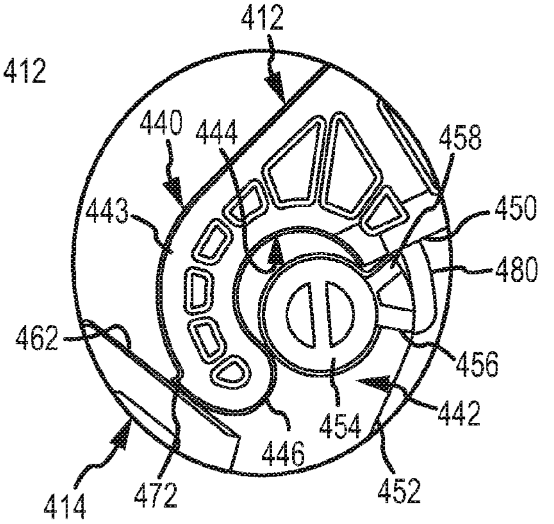
FIG. 16 is an enlarged view of the hinge of the clamp of FIG. 13 during assembly.

Another exemplary implementation of a clamp 400 with a tether 480 between the first and second arcuate members 412, 414 is illustrated in FIGS. 13-18. The tether 480 holds the first and second arcuate members 412, 414 of the clamp 400 together in the unassembled, tethered configuration of FIG. 13. In this design, the first and second arcuate members 412, 414 may be manufactured as a single unit (e.g., molded together in a single injection mold) and stay together for packaging and shipping purposes. Upon assembly, the tether 480 may be broken apart from one of the first and second arcuate members 412, 414 (see FIG. 14) enabling the clamp 400 to operate in the manner described above in connection with FIGS. 1-7. While the tether 480 may be provided on the clamp 400 configured as an external latched clamp, like the configuration of the clamp 100, the tether 480 may be provided on a clamp configured as an internal latched clamp, like the configuration of the clamp 200. The tether 480 may be formed of the same material as the clamp 400 and thus may be relatively rigid. However, the tether 480 may also be formed thin enough that it is also bendable or pliable under lateral forces or torque at its ends The clamp 400 may be assembled in the manner illustrated in FIGS. 15-18, which shows enlarged views of the barrel structure 440 of the first arcuate member 412 and the pin structure 442 of the second arcuate member 414 of the clamp 400. FIG. 15 is an enlarged view of the clamp 400 with the tether 480 in the unassembled, tethered configuration depicted in FIG. 13. The tether 480 may be coupled to the clamp 400 between the pin structure 442 and the barrel structure 440. In particular, the tether 480 may be formed as an extension of the locking ridge 472 on each of the posts 454 and may attach to the stop faces 460 on the arcuate fingers 443 of the barrel structure 440. The barrel structure 440 of the first arcuate member 412 and the hinge structure 442 of the second arcuate member 414 may be moved towards one another so that the pin-receiving recesses 444 of the barrel structure 440 cradles around the posts 454 and the arcuate fingers 443 slide between the posts 454 and the stop face 462 as illustrated in FIG. 16. As the barrel structure 440 begins to engage with the posts 454, the tether 480 may bend or flex at its connection with the stop ridge 456. The tether 480 may aid in rotating the first arcuate member 412 relative to the second arcuate member 414 and may facilitate seating the barrel structure 440 about the posts 454 to form the hinge assembly 416.

Figure 17:
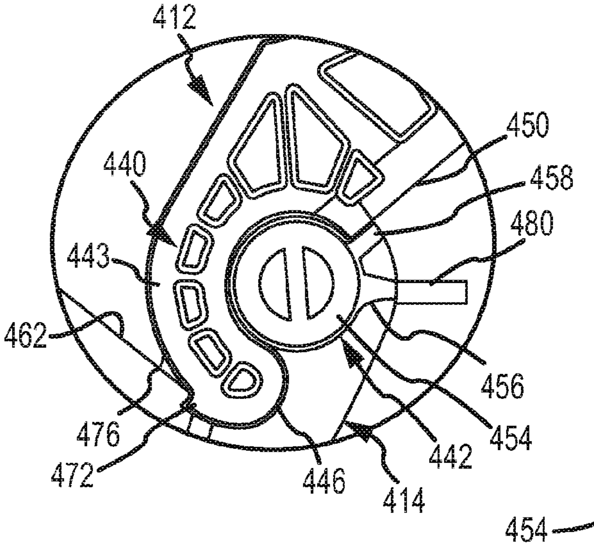
FIG. 17 is an enlarged view of the hinge of the clamp of FIG. 13 after assembly in the open position.
Figure 18:
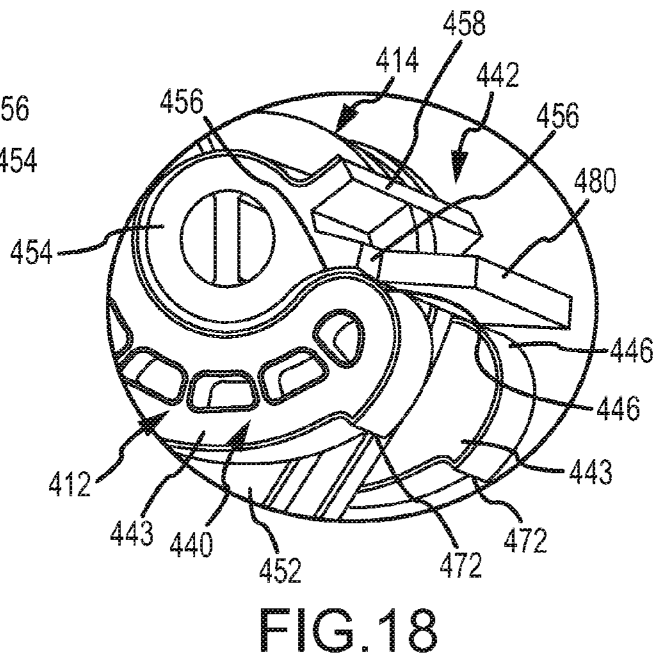
FIG. 18 is an enlarged view of the hinge of the clamp of FIG. 13 after assembly in the closed position.

Upon insertion of the arcuate fingers 473 between the posts 454 and the stop face 462 of the second arcuate member 414, the tether 480 may be designed to break apart from the barrel structure 440 as shown in FIG. 17. As illustrated in FIG. 17, the tether 480 may extend from the stop ridge 456 of the posts 454. However, it may be appreciated that the tether 480 may alternatively break apart from the stop ridge 456 and extend from the second rotational stop 450 on the barrel structure 440 of the first arcuate member 412. Upon the tether 480 detaching from the pin structure 442 or the barrel structure 440, the clamp 400 may operate in the manner described above in connection with FIGS. 1-7 to assume the closed, latched position of the clamp 400 illustrated in FIGS. 14 and 18. The detached tether 480 may be positioned relative to the components of the clamp 400 so that the operation of the hinge 416 may not impeded by the tether 480.

Figure 19:
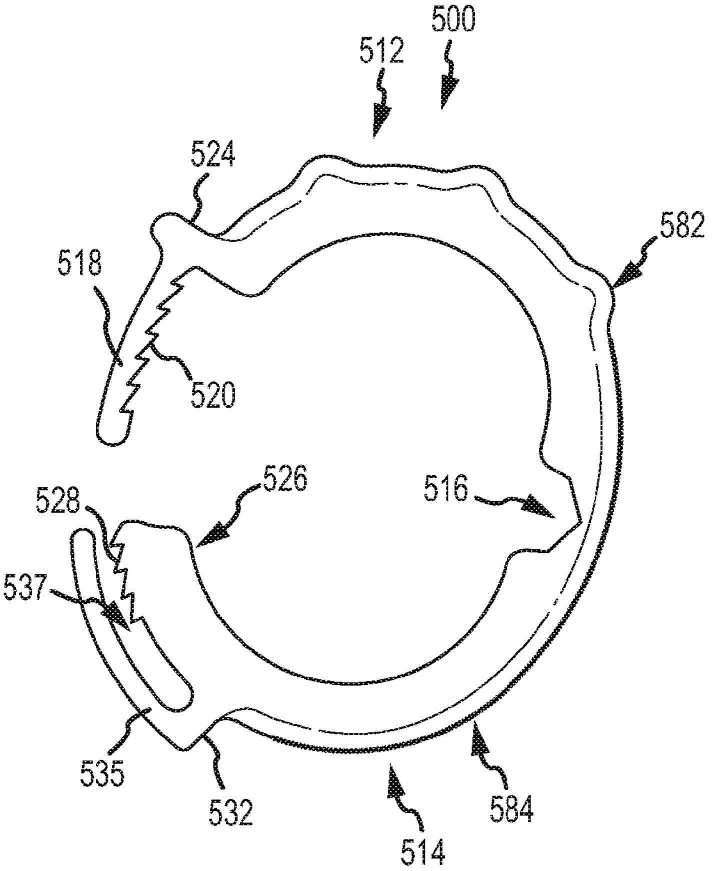
FIG. 19 is a side elevation view of another implementation of a clamp in an open position.
Figure 20:
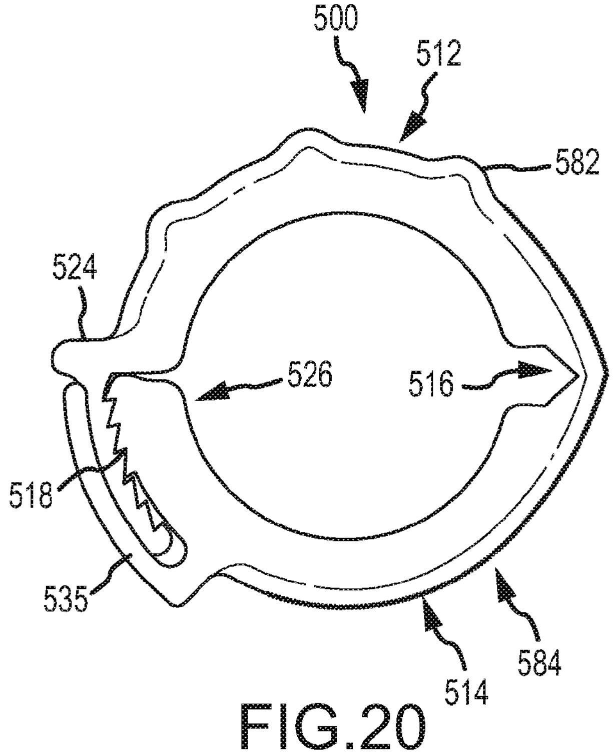
FIG. 20 is a side elevation view of the clamp of FIG. 19 in the closed position.

Turning to FIGS. 19 and 20, another exemplary implementation of a clamp 500 is illustrated with an external latch configuration. The clamp 500 differs from the previous embodiments in its unitary construction and use of a living hinge 516 joining the first arcuate member 512 to the second arcuate member 514. The clamp 500 may include finger grips 582 protruding as nodules from along an external surface of either or both of the first arcuate member 512 and the second arcuate member 514 (not shown). Other surface structures 584 such as ridges or knurls for providing a friction grip for a user's palm, fingers, or other portion of the user's hand on either or both of the second arcuate member 514 and the first arcuate member 512. When the clamp 500 is gripped between the finger grips 518 and the surface structures 520, these features may facilitate moving the clamp 500 from the open position of FIG. 19 to the closed, latched position of FIG. 20.

The clamp 500 may additionally include pliers grips 524, 532 protruding respectively from the outer diameter surfaces of the first and second arcuate members 512, 514 proximate the latch finger 518 and the mating end 526 and may facilitate movement of the clamp 500 to the closed, latched position of FIG. 20. The clamp 500 may be similar to the clamp 100 in other respects and may include, for example, a latch finger 518 with teeth 520 oriented radially inward and a mating end 526 with teeth 528 on an outer wall oriented radially outward into retention cavity 537 shielded by an enclosure wall 535 for establishing the closed, latched position. Accordingly, it may be appreciated that the structures and functions of the of the latch 500 may be provided interchangeably with the clamp 100, 300 and 400. For example, the pliers grips 524, 532 may be provided on clamp 100, which may be in addition to or as an alternative to the handles 124, 132 of the clamp 100. In addition, the clamp 500 may be configured with an internal latch configuration such as the clamp 200, and therefore the structures and functions of the clamp 500 may be provided interchangeably with the clamp 200.

Figure 21:
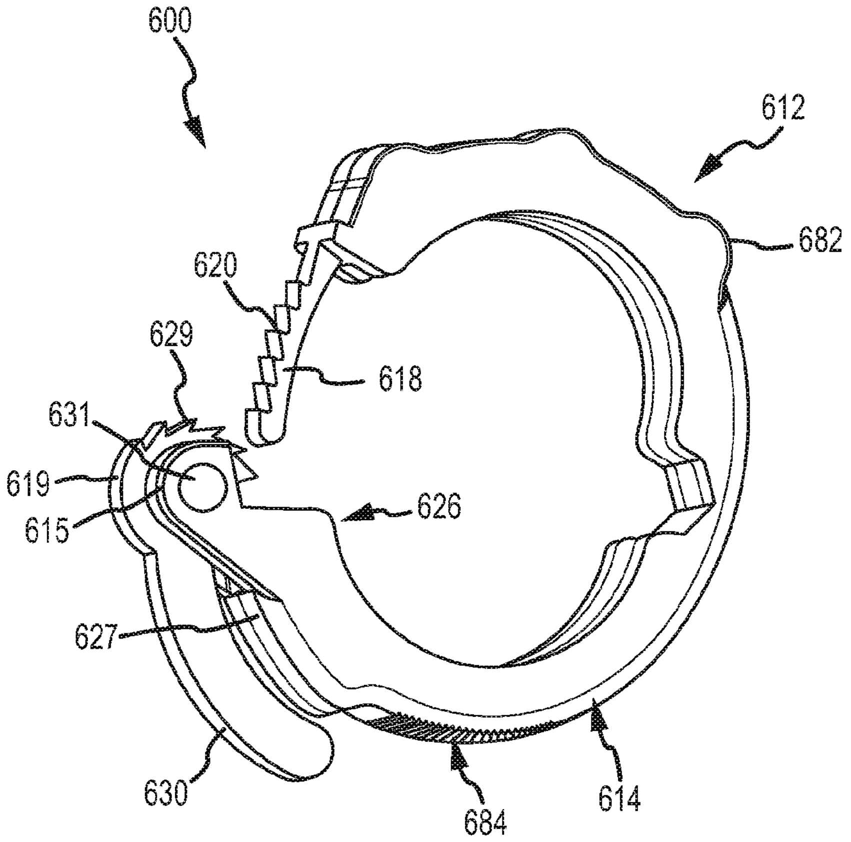
FIG. 21 is a front isometric view of another implementation of a clamp in an open position.
Figure 22:
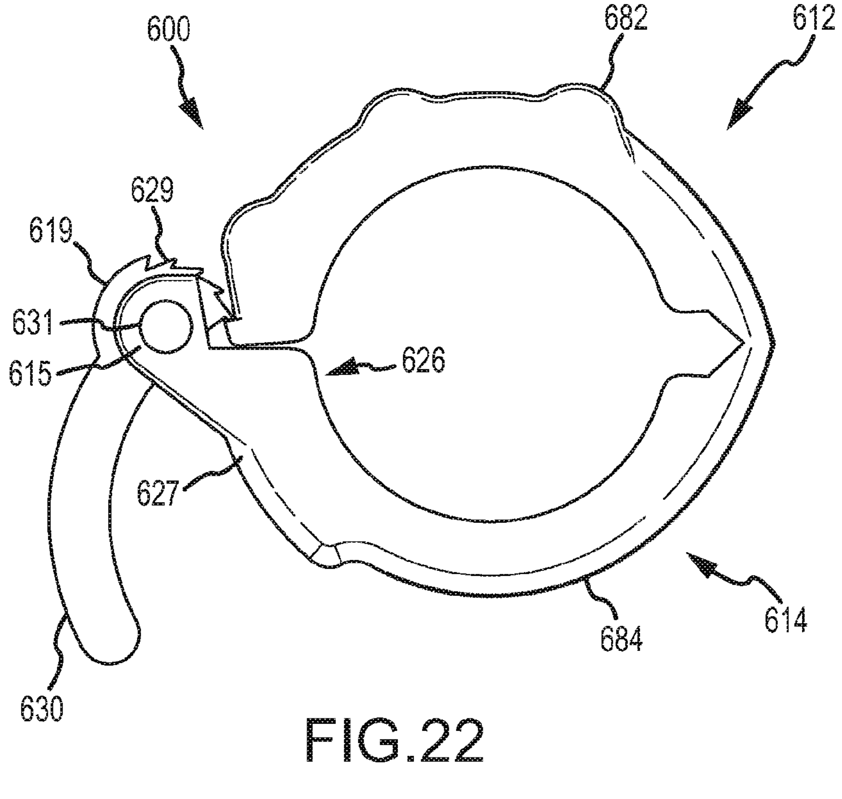
FIG. 22 is a side elevation view of the clamp of FIG. 21 in the closed position.
Figure 23:
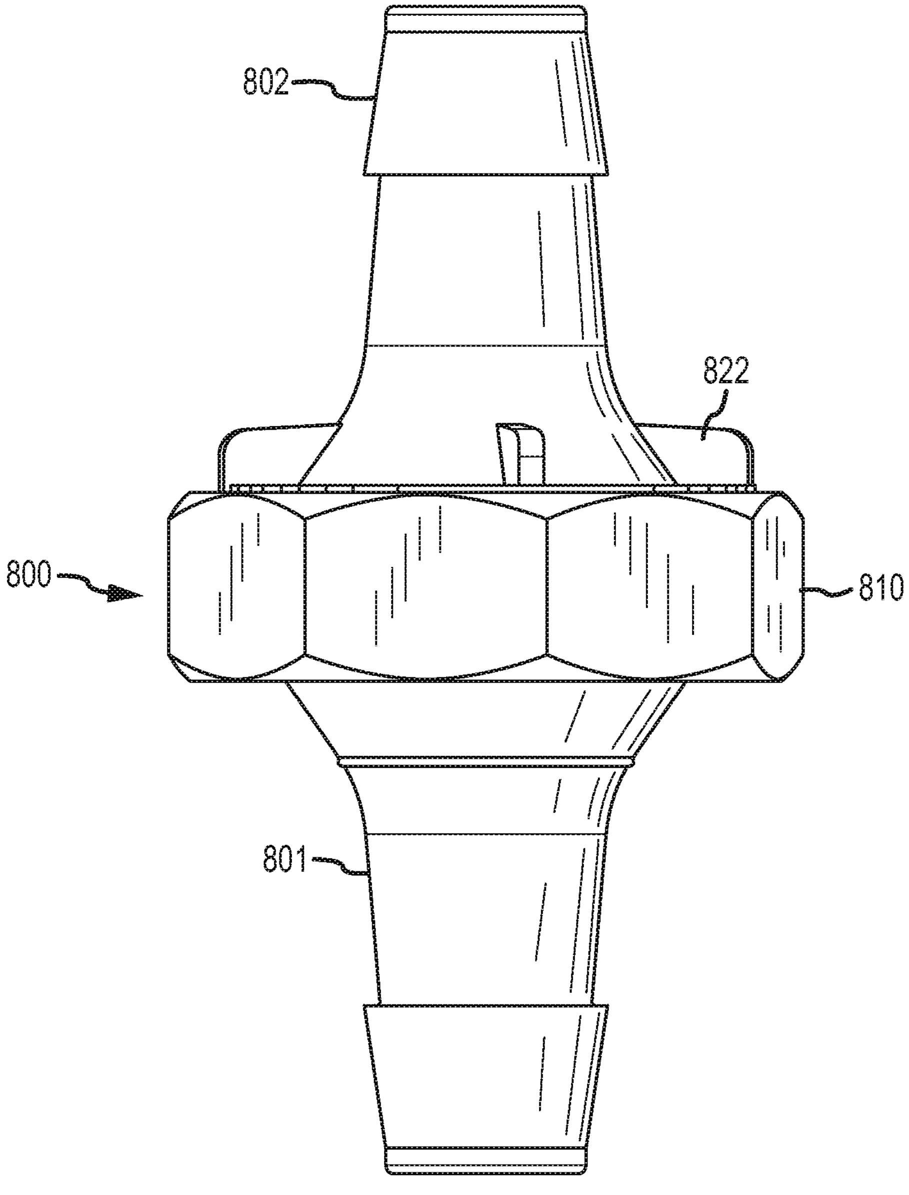
FIG. 23 is a side elevation view of another implementation of a clamp assembled with sanitary fittings.

Turning to FIGS. 21 and 22, another exemplary embodiment of clamp 600 is provided that may include a ratchet-type lever 630 for establishing a closed, latched position of the clamp 600. The clamp 600 may be configured as an internal latched clamp such as the clamp 200, and similar structures of the clamp 600 are identified with similar reference numbers as the clamp 200. The ratchet-type lever 630 may be pivotally disposed on the mating end 626 of the second arcuate member 614. The ratchet-type lever 630 enables the clamp 600 to be latched by actuating the ratchet-type lever 630 to draw the latch finger 618 of the first arcuate member 612 into the mating sleeve 627 without the use of tools such as pliers. A pair of forked arms 615 may extend from the mating end 626 of the second arcuate member 614 and hold a pivot pin 631 therein. The ratchet-type lever 630 may be attached to the forked arms 615 by the pivot pin 631 and rotate thereon. A plurality of ratchet teeth 629 may be formed on a shoulder 619 of the lever 630 adjacent the interface with the pivot pin 631.

A user may actuate the ratchet-type lever 630, and the teeth 629 of the ratchet-type lever 630 may force the teeth 620 of the latch finger 618 into the mating sleeve 627 until the teeth 620 of the latch finger 618 engage with the teeth 628 (not shown) within the mating sleeve 626. Continued rotation of the ratchet-type lever 630 may cause the teeth 620 to engage the teeth in the mating sleeve 626 as the first and second arcuate members 612, 614 are moved towards the closed, latched position of FIG. 22. In this embodiment, the ratchet-type lever 630 may help force the latch finger 618 into engagement within the mating sleeve 624 in implementations in which a higher torque is required to make a gasket seal and close and latch the clamp 600. To release the engagement, a user may insert a tool such as a screwdriver into an opening (not visible) defined in an external wall of the mating sleeve 627 to push the latch finger 618 radially inwardly in order to disengage the teeth 620 from the teeth 628 of the mating sleeve 627.

Turning to FIGS. 23-26, another exemplary implementation of a clamp system 800 is shown with a threaded joint configuration that may be used to join two sanitary fittings. The clamp system 800 may be composed of a first fitting 801, a second fitting 802, and a collar 810. The first fitting 801 may have a barbed end and a flange 818 on an opposite end for mating with another sanitary fitting. The second fitting 802 may also have a barbed end and a flange wall 824 on an opposite end for mating with another sanitary fitting. The outer surface of the flange wall 824 defines an external threaded surface 820. A number of grip fittings 822 may extend radially and axially from a top outer surface of the flange wall 824. With reference to FIG. 24, the collar 810 may include an interior with a threaded internal surface 812 extending along a portion of an inner diameter wall of the collar 810. A rim 814 may project radially inward at one end of the collar 810 and may have an internal diameter that enables an exterior (e.g., a barbed hose connector end) of the first sanitary fitting 801 to pass through the collar 810 up to a circular flange 818 extending radially outward from the first sanitary fitting 801. An annular lip 816 may extend axially from the rim 814 adjacent the inner diameter edge of the rim 814, which defines a surface on which the circular flange 818 of the first sanitary fitting 801 may be supported.

Figure 25:
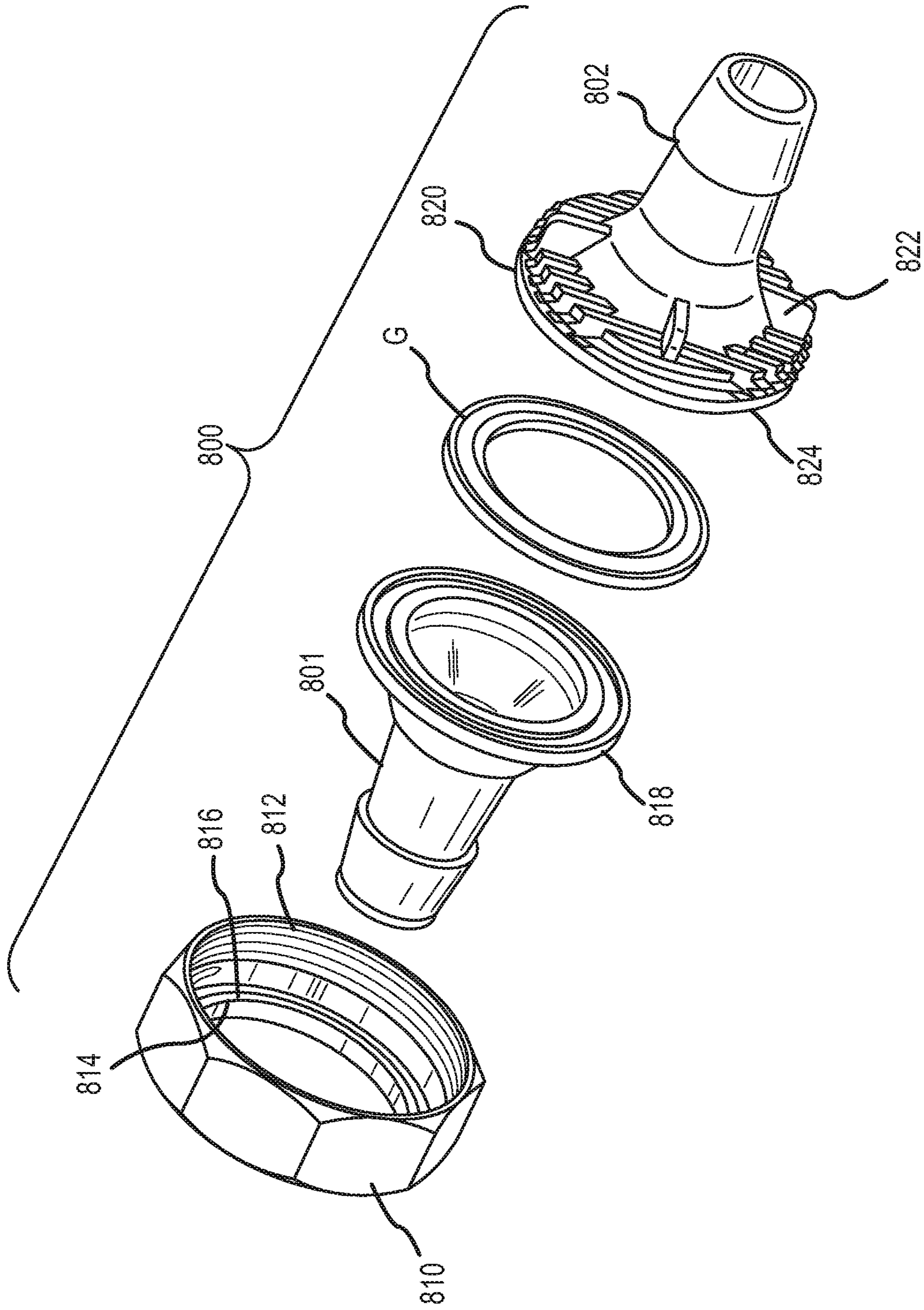
FIG. 25 is an exploded right isometric view of the clamp, the sanitary fittings, and the gasket of FIG. 23.
Figure 26:
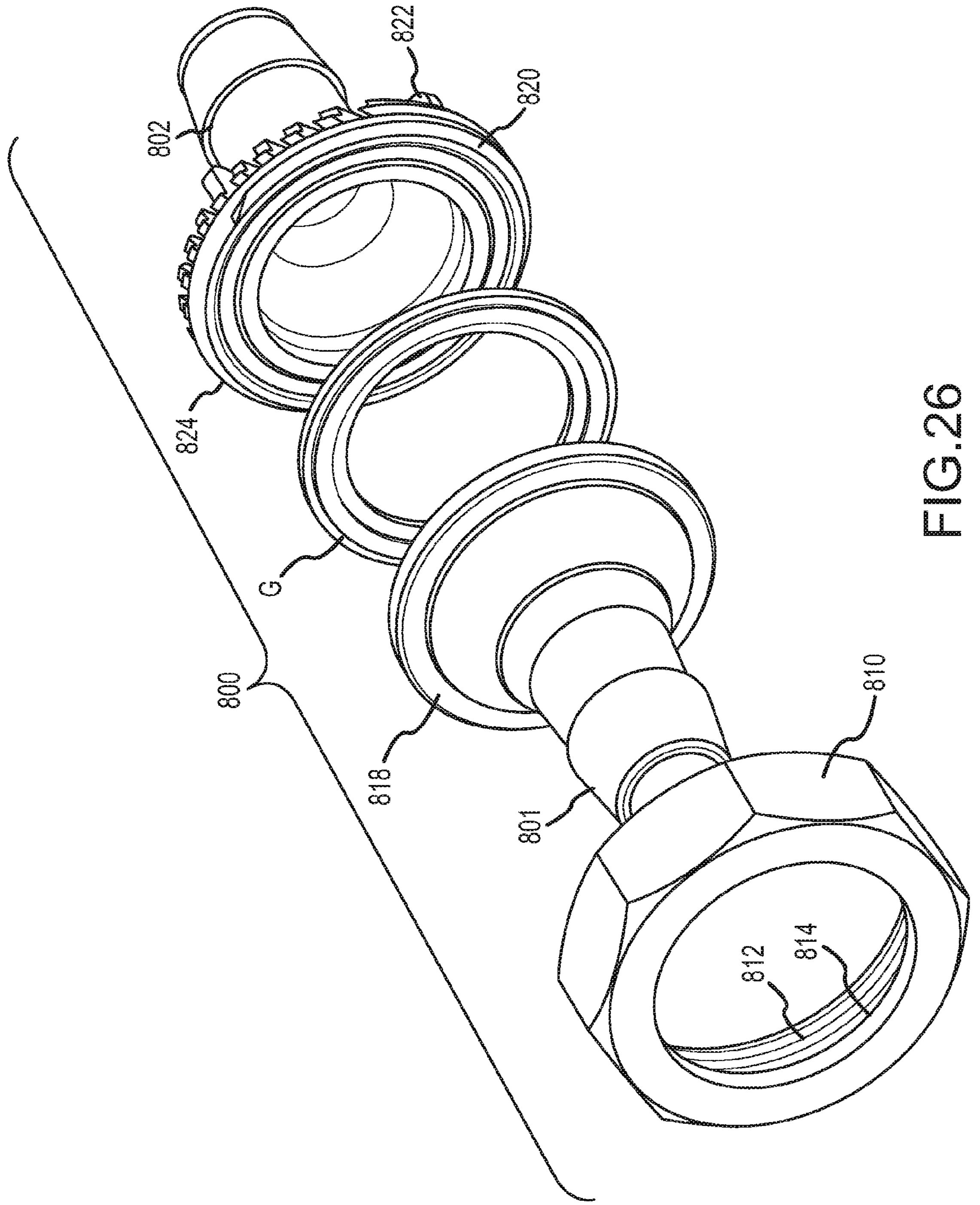
FIG. 26 is an exploded left isometric view of the clamp, the sanitary fittings, and the gasket of FIG. 23.

FIGS. 25 and 26 show exploded right side and left side views, respectively of the clamp 800, the sanitary fittings 810, 802 and the gasket G. To assemble the clamp system 800 with the sanitary fittings 801, 802, and a gasket G, a user may insert the first sanitary fitting 801 through the collar 810 until a bottom face of the flange 818 is supported by the protruding ring 816 of the collar 810. The gasket G may be positioned on a mating face 819 of the flange 818 of the first sanitary fitting 801. The second sanitary fitting 802 may then be threaded onto the collar 810. The threaded exterior surface 820 of the flange wall 824 of the second sanitary fitting 802 interfaces with the threaded internal surface 812 of the collar 810. As the collar 810 is rotated with respect to the sanitary fittings 801, 802 the mating surface 821 of the flange wall 824 of the second sanitary fitting 802 may abut the gasket G. Continued rotation of the collar 810 creates a fluid-tight seal between the flange 810 and the flange wall with the gasket G in between the mating surfaces 819, 821. Relative rotation may be facilitated by exerting rotational forces on the grip wings 822 of the second sanitary fitting 802 and the faceted surfaces of the collar 810. The collar 810 may be configured for gripping by a user's hand or by tools, such as a wrench, and may include a series of flat faces on its outer diameter wall.

Figure 27:
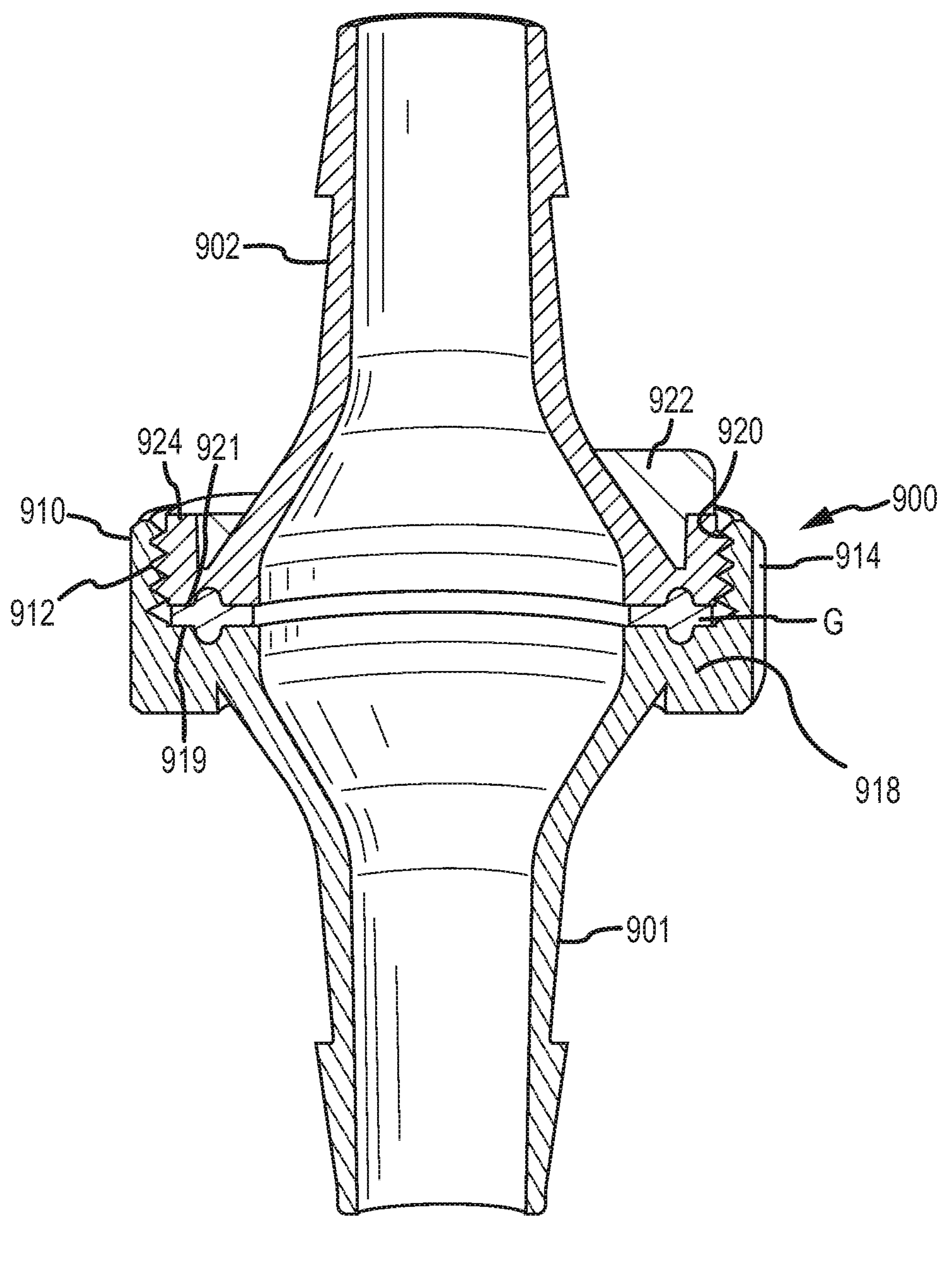
FIG. 27 is a cross-section view of another implementation of a clamp assembled with a sanitary fitting and a gasket.
Figure 28:
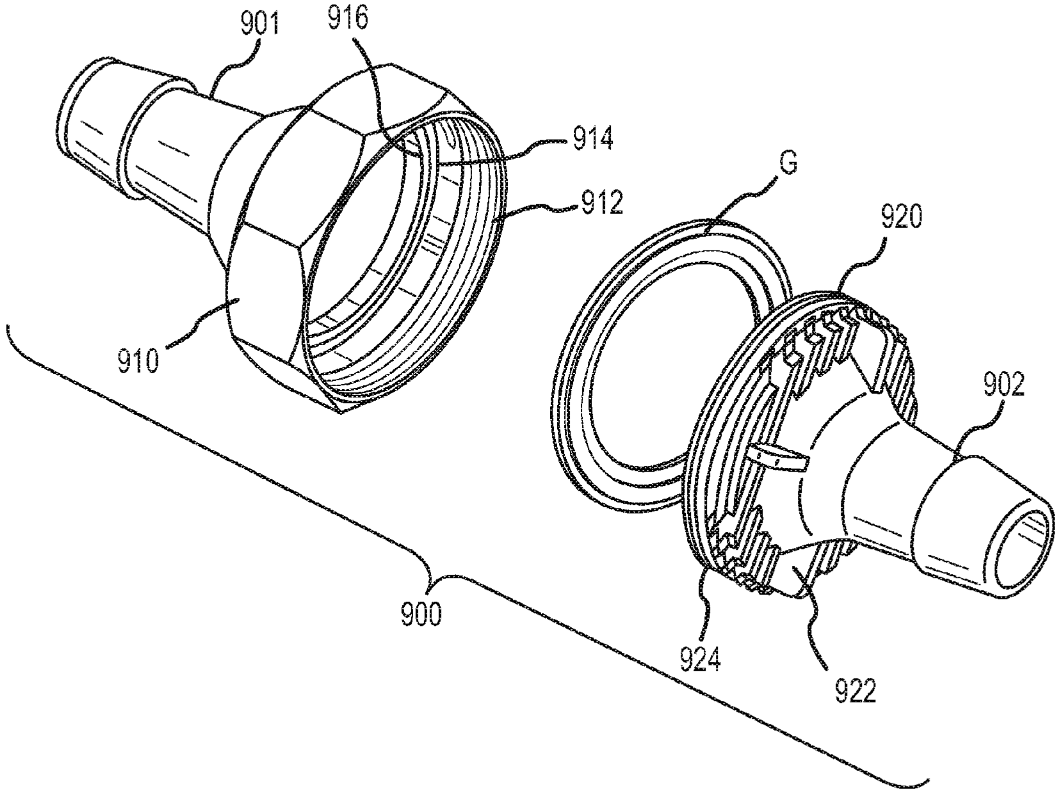
FIG. 28 is an exploded right side isometric view of the clamp, the sanitary fitting, and the gasket of FIG. 27.

Turning to FIGS. 27 and 28, another exemplary implementation of a clamp system 900 with a threaded joint configuration is depicted that may be used to join two sanitary fittings. The clamp system 900 may include a first fitting 901 threaded collar 910. The external surface of the collar 910 may be configured for gripping and may have a series of flat faces. The collar 910 may be formed as a ring-shaped flange 918 extending from an outer wall at one end of the first sanitary fitting 901. A cylindrical wall 914 may extend axially from a base of the ring-shaped flange 918 and may have a threaded internal surface 912. The second fitting 902 may have a barbed end and a flange wall 924 on an opposite end for mating with the collar 910 of the first fitting 901. The outer surface of the flange wall 924 defines an external threaded surface 920. A number of grip wings 922 may extend radially and axially from a top outer surface of the flange wall 924.

To assemble the clamp system 900 with the gasket G and the sanitary fittings 901, 902, the gasket G may be inserted into an interior of the collar 910 of the first sanitary fitting 901 so that the gasket G is supported by a mating face 919. The second sanitary fitting 902 may then be threadedly received within the collar 910. The threaded exterior surface 920 of the flange wall 924 of the second sanitary fitting 902 interfaces with the threaded internal surface 912 of the collar 910. The two sanitary fittings 901, 902 may be rotated relative to each other until the mating surface 921 of the flange wall 924 of the second sanitary fitting 902 abuts the gasket G. Relative rotation may be facilitated by exerting rotational forces on the grip wings 922 of the second sanitary fitting 902 and the faceted surfaces of the collar 910.

The clamps 100, 200, 400, 500, 600, 800 and 900 may each be operated by hand without the need to use clamping tools such as pliers to close the arcuate members, and may be configured to receive any type of sanitary fitting, such as those used in pharmaceutical, biological, and/or biopharmaceutical applications. The clamps may be configured for a single-use, or limited use, such as 2, 5, 10, or 20 opening and closing cycles or attachment and detachment procedures. The clamps may also be constructed of a rigid material such as a glass filled or glass infused Nylon or Kynar and may be formed through an injection molding process or other molding process. In addition, the clamps may be configured to exceed 160 psi clamping pressure, have a gamma radiation stability of 50 Kgy, be autoclavable (e.g., up to approximately 134° C.), and be crush resistant up to 100 lbs. While the clamps herein are described as being used in connection with sanitary fittings, it may be understood that the clamps may be used to join other structures or devices such as caps, tubes, valves, bags, vessels, and so on, that may be configured with a flange or a threaded outer surface, for example.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A clamp comprising a first arcuate member having a first stop face;

a second arcuate member having a second stop face; and a hinge assembly adjacent the first stop face and the second stop face, the hinge assembly detachably coupling the first arcuate member to the second arcuate member and enabling relative rotation between the first and the second arcuate members from an open position to a closed position; wherein the hinge assembly comprises at least one arcuate finger extending from an end of the first arcuate member and having a locking ridge formed on the outer edge of the arcuate finger;

a pin-receiving recess formed by the arcuate finger;

a post integrally formed on an end of the second arcuate member; wherein upon assembly, the arcuate finger cradles around the post and the post fits within the post-receiving recess; wherein when the clamp is in a closed position, the first stop face abuts the second stop face to provide a complete enclosure by the clamp adjacent to the hinge assembly and prevent overtightening of the clamp; and the locking ridge interfaces with a boundary edge defining a boundary of the second stop face to impede further rotation of the first arcuate member with respect to the second arcuate member from the closed position to an open position.

2. The clamp of claim 1 further comprising a latch finger extending from one of the first and second arcuate members at an end opposite the hinge assembly;

a retention cavity formed within another of the first and second arcuate members at an end opposite the hinge assembly configured to receive and engage the latch finger when the clamp is in a closed position.

3. The clamp of claim 2, wherein the latch finger defines a plurality of teeth extending radially inward;

the retention cavity defines a plurality of teeth extending radially outward from an inner wall of the retention cavity; and when the clamp is in a closed position, one or more of the teeth on the latch finger engage one or more of the teeth on the inner wall within the retention cavity.

4. The clamp of claim 2, wherein the latch finger defines a plurality of teeth extending radially outward;

the retention cavity defines a plurality of teeth extending radially inward from an outer wall within the retention cavity; and when the clamp is in a closed position, one or more of the teeth on the latch finger engage one or more of the teeth on the outer wall of the retention cavity.

5. The clamp of claim 2, wherein one of the first and the second arcuate members defines a latch release opening configured to provide access to the latch finger for releasing the latched engagement.

6. The clamp of claim 5 further comprising a first handle formed on the first arcuate member at an end opposite the hinge assembly; and a second handle formed on the second arcuate member at an end opposite the hinge assembly, wherein the latch release opening is defined in one of the first handle or the second handle.

7. The clamp of claim 5, wherein the latch release opening is defined in a wall of the first or second arcuate portion to provide access to the retention cavity.

8. The clamp of claim 1, wherein the arcuate finger is sized in width to fit between the post and the second stop face on the second arcuate member and an outer edge of the arcuate finger is configured slide along the second stop face while the pin-receiving recess slides about the post when the clamp is opened and closed.

9. The clamp of claim 1, wherein a biasing ridge is formed on the outer edge of the arcuate finger spaced apart from the locking ridge; and when the locking ridge abuts the boundary edge, the biasing ridge interfaces with a surface of the second stop face to frictionally hold the first arcuate member in a fixed position with respect to the second arcuate member, thereby holding the clamp in an open position.

10. The clamp of claim 9, wherein the second arcuate member further defines an undercut beneath the second stop face adjacent the boundary edge to define a lip extension that flexes to assist in receiving either or both of the biasing ridge or the locking ridge onto the second stop face.

11. The clamp of claim 9, wherein movement of the biasing ridge off the second stop face past the boundary edge enables the first and the second arcuate members to move to the closed position; and movement of the locking ridge off the stop face in a direction toward the biasing ridge causes the first and the second arcuate members to detach from one another.

12. The clamp of claim 1, wherein a stop ridge is formed on the post and abuts a rotational stop provided on the first arcuate member to halt relative rotation between the first and second arcuate members at either a closed position of the clamp or at an open position of the clamp.

13. The clamp of claim 1 further comprising a first handle formed on the first arcuate member at an end opposite the hinge assembly; and a second handle formed on the second arcuate member at an end opposite the hinge assembly;

wherein the first and second handles are configured to enable a user to rotate the first and second arcuate members relative to each other about the hinge assembly.

14. The clamp of claim 13, further comprising a first tie loop formed on the first handle and oriented toward the second arcuate member; and a second tie loop formed on the second handle and oriented toward the first arcuate member;

wherein the tie loops are configured to receive a tie device to secure the clamp in the closed position.

15. The clamp of claim 1, wherein each of the first arcuate member and the second arcuate member defines an arcuate channel along an inner diameter of each of the first arcuate member and the second arcuate member open to a center axis of the clamp when the clamp is in a closed position.

16. The clamp of claim 1 further comprising a second arcuate finger extending from the end of the first arcuate member and having a locking ridge formed on the outer edge of the second arcuate finger; and a second pin-receiving recess formed by the second arcuate finger; wherein upon assembly, the at least one arcuate finger and the second arcuate finger cradle around the post and the post fits within the pin-receiving recesses.

* * * * *